US012329361B2

(12) United States Patent
Tanigami et al.

(10) Patent No.: US 12,329,361 B2
(45) Date of Patent: Jun. 17, 2025

(54) HEAT INVASION OBSERVATION APPARATUS, ENDOSCOPE SYSTEM, HEAT INVASION OBSERVATION SYSTEM, AND HEAT INVASION OBSERVATION METHOD

(71) Applicant: OLYMPUS CORPORATION, Hachioji (JP)

(72) Inventors: Yasuo Tanigami, Shibuya-ku (JP); Yusuke Otsuka, Yokohama (JP); Noriko Kuroda, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 1128 days.

(21) Appl. No.: 17/197,949

(22) Filed: Mar. 10, 2021

(65) Prior Publication Data

US 2021/0186594 A1 Jun. 24, 2021

Related U.S. Application Data

(63) Continuation of application No. PCT/JP2019/035563, filed on Sep. 10, 2019.

(30) Foreign Application Priority Data

Sep. 10, 2018 (WO) .................. PCT/JP2018/033457

(51) Int. Cl.
*A61B 1/04* (2006.01)
*A61B 1/00* (2006.01)
(Continued)

(52) U.S. Cl.
CPC ........ *A61B 1/043* (2013.01); *A61B 1/000094* (2022.02); *A61B 1/0655* (2022.02);
(Continued)

(58) Field of Classification Search
None
See application file for complete search history.

(56) References Cited

U.S. PATENT DOCUMENTS

2001/0007921 A1* 7/2001 Hayashi ............... A61B 5/0084
600/478
2002/0002337 A1* 1/2002 Alfano ............... G01N 21/6486
250/363.01
(Continued)

FOREIGN PATENT DOCUMENTS

CN 107063978 A 9/2016
JP H10-505768 A 6/1998
(Continued)

OTHER PUBLICATIONS

Jan. 30, 2024 Office Action issued in Chinese Patent Application No. 201980055360.2.
(Continued)

*Primary Examiner* — John P Leubecker
(74) *Attorney, Agent, or Firm* — Oliff PLC

(57) ABSTRACT

A heat invasion observation apparatus that observes a heat invasion to a biological tissue, the heat invasion observation apparatus includes a fluorescence image generation circuit configured to obtain an image pickup signal generated by picking up an image of fluorescence generated from a heat invasion area in the biological tissue irradiated with exciting light for exciting a substance contained in the heat invasion area, and generate fluorescence image data based on the obtained image pickup signal. The substance contained in the heat invasion area is a substance generated when the biological tissue is thermally processed.

29 Claims, 10 Drawing Sheets

(51) Int. Cl.
*A61B 1/06* (2006.01)
*A61B 17/00* (2006.01)
*A61B 18/14* (2006.01)
*A61B 18/00* (2006.01)

(52) U.S. Cl.
CPC .. *A61B 18/148* (2013.01); *A61B 2017/00061* (2013.01); *A61B 2017/00128* (2013.01); *A61B 2018/00595* (2013.01); *A61B 2018/00773* (2013.01); *A61B 2018/00791* (2013.01); *A61B 2018/1412* (2013.01)

(56) References Cited

U.S. PATENT DOCUMENTS

| | | | |
|---|---|---|---|
| 2005/0119548 A1* | 6/2005 | Lin | A61B 5/4244 600/407 |
| 2007/0276259 A1* | 11/2007 | Okawa | A61B 5/0084 600/476 |
| 2010/0179522 A1* | 7/2010 | Companion | A61B 8/085 606/10 |
| 2011/0121200 A1* | 5/2011 | Watanabe | G01J 3/2803 250/458.1 |
| 2012/0190945 A1 | 7/2012 | Yamanaka et al. | |
| 2013/0102862 A1* | 4/2013 | Mercader | A61B 1/0676 600/317 |
| 2013/0190742 A1* | 7/2013 | Connors | A61B 18/20 606/17 |
| 2015/0141847 A1* | 5/2015 | Sarvazyan | A61B 5/0036 600/478 |
| 2015/0196202 A1* | 7/2015 | Mercader | A61B 5/0071 600/478 |
| 2017/0074795 A1 | 3/2017 | Irie | |
| 2017/0360275 A1* | 12/2017 | Yoshizaki | A61B 1/00055 |
| 2020/0261170 A1* | 8/2020 | Ziso | A61B 17/3403 |
| 2020/0367818 A1* | 11/2020 | DaCosta | A61K 41/0061 |

FOREIGN PATENT DOCUMENTS

| | | |
|---|---|---|
| JP | 2000-517053 A | 12/2000 |
| JP | 2008-229025 A | 10/2008 |
| JP | 2012-130506 A | 7/2012 |
| JP | 2016-540558 A | 12/2016 |
| JP | 2017-023604 A | 2/2017 |
| WO | 1998/009165 A1 | 3/1998 |
| WO | 2011-040599 A1 | 4/2011 |
| WO | 2015-073871 A2 | 5/2015 |

OTHER PUBLICATIONS

Nov. 26, 2019 International Search Report issued in International Application No. PCT/JP2019/035563.

* cited by examiner

HEAT INVASION OBSERVATION APPARATUS, ENDOSCOPE SYSTEM, HEAT INVASION OBSERVATION SYSTEM, AND HEAT INVASION OBSERVATION METHOD

CROSS REFERENCE TO RELATED APPLICATION

This application is a continuation application of PCT/JP2019/035563 filed on Sep. 10, 2019 and claims benefit of International Application No. PCT/JP2018/033457 filed on Sep. 10, 2018, the entire contents of which are incorporated herein by this reference.

BACKGROUND OF THE INVENTION

1. Field of the Invention

The present invention relates to a heat invasion observation apparatus that visualizes, by using an energy device or the like, a state of cautery to a subject such as a biological tissue, an endoscope system, a heat invasion observation system, and a heat invasion observation method.

2. Description of the Related Art

Up to now, for a medical endoscope mainly used in the medical field, an endoscope video scope system in which a special light observation function for emphasizing and displaying an observation target by controlling a wavelength of light is installed has been generally in practice.

For example, a narrow band light observation (Narrow Band Imaging (registered trademark) (NBI)) function realizes emphasized display of a capillary blood vessel of a mucosal superficial layer or a mucosal microscopic pattern by irradiating a subject such as a biological tissue (hereinafter, simply referred to as a subject) with light at two wavelengths (390 to 445 nm/530 to 550 nm) that are set to be narrow bands easily absorbed by hemoglobin in blood.

In addition, an infrared light observation (infra red imaging (IRI)) function realizes emphasized display of a blood vessel of a mucosal deep portion where visual recognition is difficult in a normal light observation or blood flow information by irradiating the subject with two types of infrared light (790 to 820 nm/905 to 970 nm) after an intravenous injection of an infrared index agent with which infrared light is easily absorbed.

A fluorescence observation (auto fluorescence imaging (AFI)) function realizes emphasized display of a neoplastic lesion and a normal mucosa in different color tones by irradiating the subject with exciting light (390 to 470 nm) for observing autofluorescence from the biological tissue and light at a wavelength (540 to 560 nm) absorbed in hemoglobin in blood. In other words, the fluorescence observation (AFI) function is a technology with which, by observing autofluorescence from a biological mucosa, it is possible to emphasize and display the neoplastic lesion and the normal mucosa in the different color tones.

In recent years, by using these special light observation functions, image data for an early discovery of a minute lesion such as cancer, a precise diagnosis of a lesion range before a surgery, or the like can be easily obtained, and the precise diagnosis by a doctor can be supported.

However, since these conventional special light observation functions are mainly used for observing a surface of a lesion portion, a range of the lesion portion generated on a surface of the subject can be easily figured out by a visual check too, but it is difficult to easily determine depth information or the like of the lesion portion by a visual check alone.

In view of the above, for example, up to now, various technologies for evaluating or estimating depth information of a lesion portion or an injury site based on image data obtained by the conventional special light observation functions have been proposed.

For example, Japanese Patent Application Laid-Open Publication No. H10-505768 discloses a burn injury evaluation apparatus that allows a doctor to promptly evaluate a range and a depth of a burn injury on a skin by using an induced fluorescence spectroscopy based on ultraviolet light or blue light or a reflection spectroscopy of visible light and infrared light and an evaluation method of the burn injury evaluation apparatus. The burn injury evaluation apparatus includes a plurality of light sources configured to emit exciting light at wavelengths of a plurality of predetermined types, a sensor configured to measure the amount of response light emitted from the light sources and reflected by the subject, a microprocessor, and the like, and is configured to optically evaluate a skin of a burnt area.

In addition, Japanese Patent Application Laid-Open Publication No. 2012-130506 discloses an electronic endoscope system serving as a light measurement system that enhances certainty of an estimation of an absorption component concentration, and a light measurement method of the electronic endoscope system. The electronic endoscope system is a system configured to irradiate the subject with exciting light, and excite an infrared indicator agent (indocyanine green (ICG)) injected into a blood vessel, so that based on an image pickup signal obtained by picking up an image of the blood vessel, it is possible to estimate a depth of the blood vessel from a surface of the subject.

Japanese Patent Application Laid-Open Publication No. 2008-229025 discloses a fluorescence observation apparatus that enables an accurate diagnosis of a lesion portion by precisely correcting fluorescence image data obtained by using the fluorescence observation function.

SUMMARY OF THE INVENTION

A heat invasion observation apparatus according to an aspect of the present invention is a heat invasion observation apparatus that observes a heat invasion to a biological tissue, the heat invasion observation apparatus including a fluorescence image generation circuit configured to obtain an image pickup signal. The fluorescence image generation circuit is configured to generate fluorescence image data based on the obtained image pickup signal. The image pickup signal is obtained by picking up an image of fluorescence generated from a heat invasion area in the biological tissue irradiated with exciting light for exciting a substance contained in the heat invasion area. The substance contained in the heat invasion area is generated when the biological tissue is thermally processed.

An endoscope system according to an aspect of the present invention is an endoscope system that observes advanced glycation end products (AGEs) contained in a biological tissue, the endoscope system including a light source apparatus that can generate exciting light for exciting the AGEs, an image pickup device configured to capture fluorescence generated from a substance containing the AGEs, the substance being a substance contained in a heat invasion area in the biological tissue irradiated with the exciting light and generated when the biological tissue is thermally processed, and generate an image pickup signal, and an image generation circuit configured to generate fluorescence image data based on the image pickup signal.

A heat invasion observation system according to an aspect of the present invention is a heat invasion observation system that observes a heat invasion to a biological tissue, the heat invasion observation system including a light source apparatus configured to generate exciting light for exciting a substance contained in a heat invasion area, an image pickup device configured to pick up an image of fluorescence generated from the heat invasion area in the biological tissue irradiated with the exciting light and generate an image pickup signal, and a fluorescence image generation circuit configured to generate fluorescence image data based on the image pickup signal generated by the image pickup device picking up the image of the fluorescence. The substance contained in the heat invasion area is a substance generated when the biological tissue is thermally processed.

A heat invasion observation method according to an aspect of the present invention is a heat invasion observation method of observing a heat invasion to a biological tissue, the heat invasion observation method including generating exciting light for exciting a substance contained in a heat invasion area and generated by thermal processing, generating an image pickup signal by picking up an image of fluorescence generated from the heat invasion area in the biological tissue irradiated with the exciting light, and generating fluorescence image data based on the image pickup signal generated by an image pickup device picking up the image of the fluorescence.

DETAILED DESCRIPTION OF THE PREFERRED EMBODIMENT(S)

Hereinafter, the present invention will be described by way of illustrated embodiments.

Respective diagrams used for the following explanation are schematic diagrams, and to illustrate respective components in recognizable sizes on the drawings, dimensional relationships, scales, and the like of respective parts may be varied for each of the components. Therefore, with regard to quantities of the respective components, shapes of the respective components, ratios of sizes of the respective components, relative positional relationships of the respective components, and the like described in the respective diagrams, the present invention is not limited to only the illustrated modes.

A heat invasion observation apparatus of the present invention performs a normal white light observation (white light imaging (WLI)) and a special light observation (fluorescence observation) on an area applied with a heat invasion such as cautery to a subject such as a biological tissue by using an energy device or the like, obtains normal white light image data and fluorescence image data including fluorescence intensity information, generates display image data in a predetermined mode based on the obtained white light image data and the obtained fluorescence image data, and displays an image represented by the display image data in various display modes by using a display unit (monitor). According to this, the heat invasion observation apparatus of the present invention can clearly visualize the heat invasion area by the cautery.

According to one embodiment which will be described below, as one example of the heat invasion observation apparatus, a medical endoscope system of a mode mainly used in the medical field is exemplified.

[One Embodiment]

Figure 1:
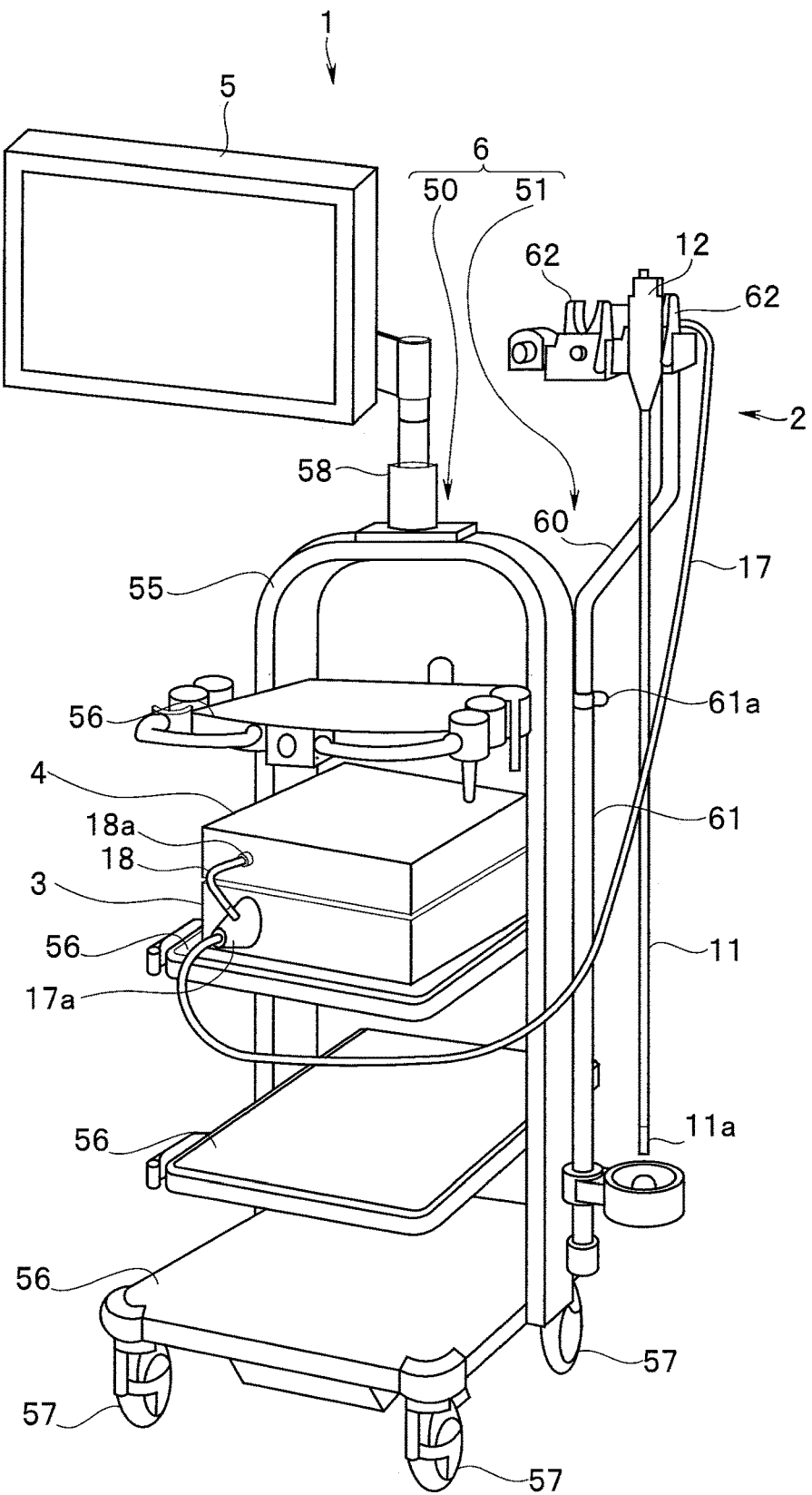
FIG. 1 is an external perspective view illustrating an entire configuration of an endoscope system serving as a heat invasion observation apparatus according to one embodiment of the present invention.
Figure 2:
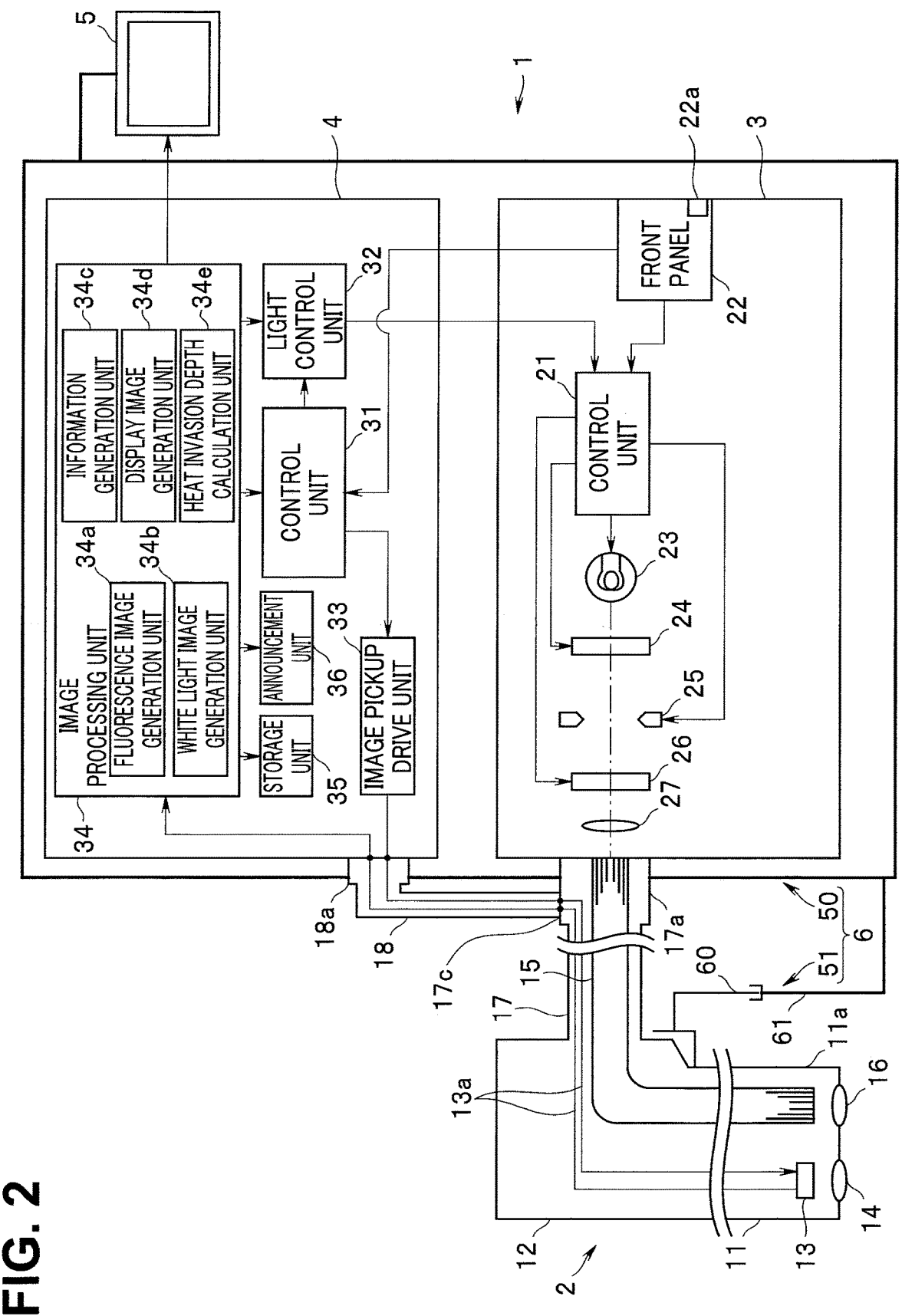
FIG. 2 is a block diagram illustrating a schematic configuration of the endoscope system of FIG. 1.
Figure 3:
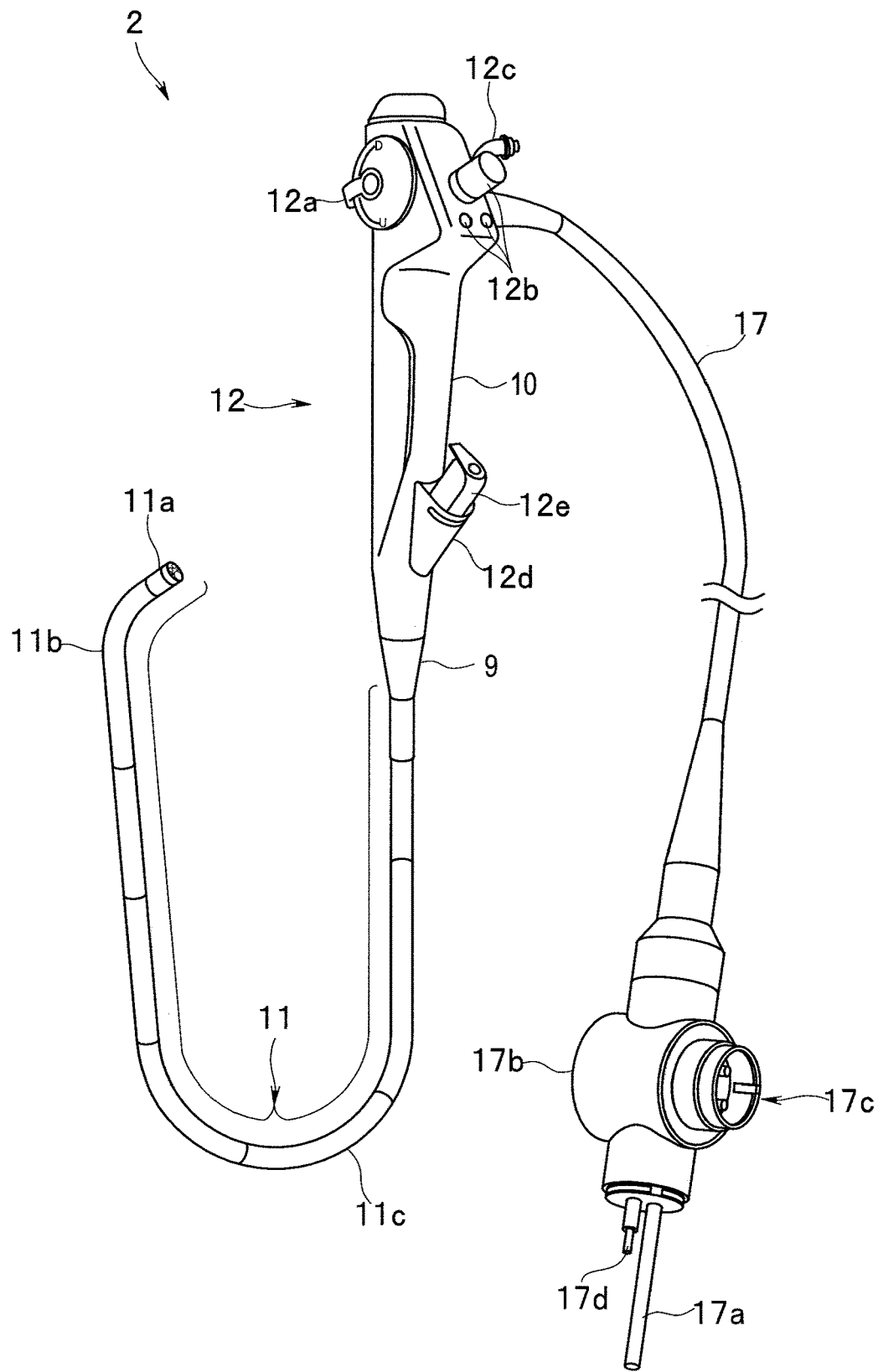
FIG. 3 is an external perspective view illustrating an endoscope included in the endoscope system of FIG. 1.
Figure 4:
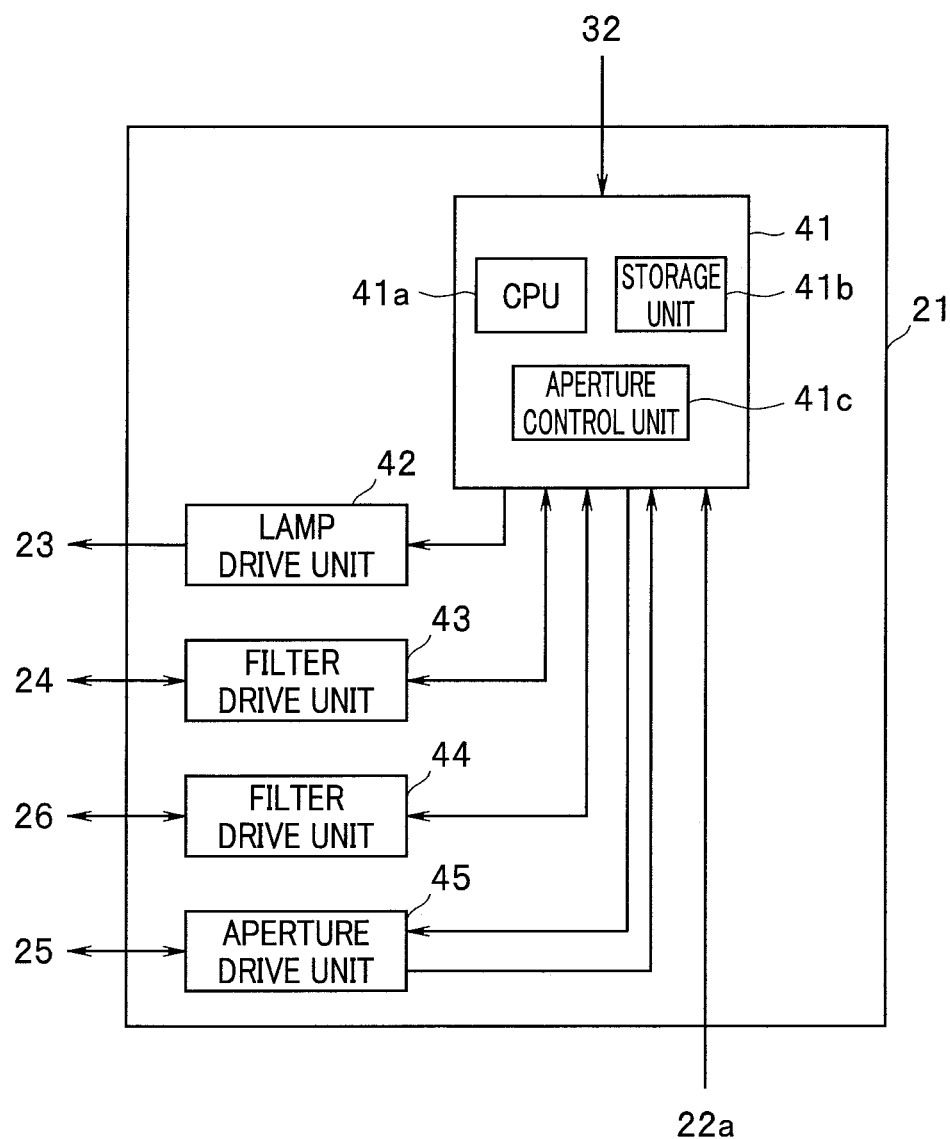
FIG. 4 is a main portion block diagram illustrating a detailed configuration of a control unit of a light source apparatus in the endoscope system of FIG. 1.

FIG. 1 is an external perspective view illustrating an entire configuration of an endoscope system serving as the heat invasion observation apparatus of one embodiment of the present invention. FIG. 2 is a block diagram illustrating a schematic configuration of the endoscope system of FIG. 1. FIG. 3 is an external perspective view illustrating an endoscope included in the endoscope system of FIG. 1. FIG. 4 is a main portion block diagram illustrating a detailed configuration of a control unit of a light source apparatus of the endoscope system of FIG. 1.

An endoscope system 1 including the heat invasion observation apparatus of one embodiment of the present invention is configured, as illustrated in FIG. 1 and FIG. 2, by including an endoscope 2, a light source apparatus 3, a video processor 4, a monitor 5, a medical trolley 6 (not illustrated in FIG. 2) which holds these components, and the like.

First, the endoscope 2 is mainly configured, as illustrated in FIG. 1 to FIG. 3, by including an elongate insertion portion 11, an operation portion 12, a universal cable 17, an endoscope connector 17b, and the like.

The insertion portion 11 is a tubular member that is formed into an elongated tubular shape and inserted into the subject. The insertion portion 11 is formed in a manner that a distal end portion 11a, a bending portion 11b, and a flexible tube portion 11c are continuously disposed in the stated order from a distal end side, and has flexibility as a whole.

Inside the distal end portion 11a among the portions, as illustrated in FIG. 2, an image pickup device 13 constituted by an image sensor such as a CCD, an objective optical system 14 configured to form an optical image of the subject on the image pickup device 13, one end of a light guide 15 constituted by optical fiber inserted into the insertion portion 11, an illumination optical system 16 serving as an irradiation unit configured to irradiate an observation target (subject) with illumination light guided by the light guide 15, and the like are arranged.

The bending portion 11b is a mechanism unit configured such that the bending portion 11b may be actively bent in two directions including up and down in response to a turning operation of a bending operation lever 12a serving as a bending operation member configured to operate a bending operation among a plurality of operation members (described below) disposed in the operation portion 12.

Note that a mode of the bending portion in the endoscope to which the present invention may be applied is not limited to the above-described one example (type in which bending can be performed in the two directions of up and down), but may also be a type in which bending may be performed in four directions also including left and right directions in addition to the up and down directions (that is, in all circumferential directions around a shaft of the insertion portion 2 by respective separate operations in up and down and left and right directions) or the like.

The flexible tube portion 11c is a tubular member formed to have bendability to be passively flexible. In addition to a treatment instrument insertion channel (not illustrated), various electric signal lines 13a extending from the image pickup device 13 built in the distal end portion 11a and passing through the inside of the operation portion 12 to be extended and disposed into the inside of the universal cable 17, the light guide 15 that guides light emitted from the light source apparatus 3 (described below) serving as an external device into the illumination optical system 16 disposed on a distal end surface of the distal end portion 11a, and the like are inserted inside the flexible tube portion 11c.

The operation portion 12 is a configuration unit continuously disposed to a proximal end portion of the insertion portion 11, and configured by including a plurality of operation members and the like. The operation portion 12 is configured by a bend preventing portion 9, a grasping portion 10, a plurality of operation members (12a, 12b, and the like), a treatment instrument insertion portion 12d, a suction valve 12c, and the like.

The bend preventing portion 9 is a protection member disposed in a connection part between a distal end part of the operation portion 12 and a proximal end part of a flexible tube portion 8, and configured to prevent unnecessary and abrupt bend of the flexible tube portion 8 when the endoscope 2 is used by covering the proximal end part of the flexible tube portion 8.

The grasping portion 10 is a casing portion that accommodates inside thereof various configuration members. The grasping portion 10 is continuously disposed to the bend preventing portion 9. The grasping portion 10 is a part grasped by a hand of a user when the endoscope 2 is used.

The treatment instrument insertion portion 12d is a configuration portion that includes a treatment instrument insertion opening (not illustrated) for inserting various treatment instruments (not illustrated), and is provided with a treatment instrument insertion path that communicates with the treatment instrument insertion channel inside the operation portion 12. In the treatment instrument insertion portion 12d, a forceps stopper 12e that serves as a lid member for opening and closing the treatment instrument insertion opening and is configured to be detachably attached to the treatment instrument insertion portion 12d is arranged.

In addition, as illustrated in FIG. 3, the bending operation lever 12a, various switches 12b, the suction valve 12c, and the like are disposed in the operation portion 12. Among the parts, the bending operation lever 12a is an operation member configured to perform a bending operation of the bending portion 11b. In addition, the various switches 12b include, for example, an operation member configured to perform an air/water feeding operation or a suction operation, and an operation member configured to perform operations respectively corresponding to an image pickup unit, an illumination unit, and the like.

The suction valve 12c is a joining portion for joining a suction tube path with a suction apparatus that is not illustrated in the drawing.

The universal cable 17 extends from a side portion on a proximal end side of the operation portion 12. The universal cable 17 is a hollow tubular member having flexibility and extending from the operation portion 12. As illustrated in FIG. 2, the universal cable 17 is a composite cable in which the light guide 15, the electric signal lines 13a extending from the image pickup device 13, and the like are inserted.

A connector 17b serving as a connection terminal with another device is disposed in an extending end portion of the universal cable 17. A light source connector 17a connected to be detachably attached to the light source apparatus 3 on the distal end side, an air/water feeding plug 17d configured to connect an air/water feeding tube (not illustrated) from an air/water feeding apparatus (not illustrated) serving as an external device, and the like are disposed in the connector 17b (see FIG. 1 to FIG. 3).

In addition, an electric connector 17c (see FIG. 2 and FIG. 3) to which a scope cable 18 (see FIG. 1 and FIG. 2; not illustrated in FIG. 3) is connected is disposed in the connector 17b, the scope cable 18 being electrically connected to the electric signal lines 13a.

In addition, a signal connector 18a (see FIG. 2) detachably connected to the video processor 4 is disposed in an extending end of the scope cable 18.

Next, the light source apparatus 3 is a light source unit including a function for respectively separately generating exciting light and white light as the illumination light to be irradiated to the observation target (subject).

As illustrated in FIG. 2, the light source apparatus 3 is configured by including a control unit 21, a front panel 22, a lamp 23 serving as a light source, a first rotation filter 24, an aperture apparatus 25, a second rotation filter 26, a condenser lens 27, and the like.

The control unit 21 is configured to perform overall control of the light source apparatus 3, and also control of the lamp 23 and the aperture apparatus 25 based on signals related to brightness from the video processor 4. The control unit 21 is configured by including a central processing unit (CPU), a ROM, a RAM, and the like. Note that a detailed configuration of the control unit 21 will be described below.

An observation mode switching switch 22a configured to switch various observation modes (such as a white light (normal light) observation mode, a fluorescence (special light) observation mode, and a marking check mode), various other operation switches (not illustrated), and the like are provided on the front panel 22. An operation signal from the front panel 22 is inputted to the control unit 21.

The observation mode switching switch 22a is a switching switch configured to instruct switching of an illumination mode corresponding to the normal light observation mode and an illumination mode corresponding to the special light observation mode.

Note that the light source apparatus 3 is configured in a manner that at least the white light for a normal light observation and the exciting light serving as light in a specific wavelength band for the special light observation can be generated.

The lamp 23 is a light source configured to supply the illumination light to the subject, and for example, a xenon lamp or the like is applied. On and off control of the lamp 23 is performed according to drive signals from the control unit 21.

The first rotation filter 24 is filter used for selectively emitting one of the light in the wavelength band for the normal light observation and the light in the wavelength band for the special light observation. The first rotation filter 24 turns about a rotation shaft of the first rotation filter 24 based on a control signal from the control unit 21, and operates to arrange the filter according to the mode specified by the observation mode switching switch 22a on a light path of the emitted light of the lamp 23.

The first rotation filter 24 is an optical filter that is disposed to be detachably inserted in the light path of the light emitted by the lamp 23, and transmits, at the time of the special light observation mode, light in a part of the band of the light at the time of the normal light observation mode in a state where the first rotation filter 24 is inserted in the light path.

Therefore, according to this, at the time of the special light observation mode, the lamp 23 and the optical filter of the first rotation filter 24 constitute the light source. In other words, at the time of the special light observation mode, the light source apparatus 3 inserts the optical filter in the light path, and supplies the light transmitted through the optical filter to the light guide 15 as the illumination light.

The aperture apparatus 25 is a light amount adjustment apparatus configured to adjust the emitted light amount of the illumination light supplied to the light guide 15. When the aperture apparatus 25 is driven in a direction for closing the aperture or in a direction for opening the aperture based on an aperture drive signal from the control unit 21, the light amount of the emitted light of the lamp 23 is adjusted.

The second rotation filter 26 is a filter unit configured by including, for example, a red (R) filter, a green (G) filter, and a blue (B) filter to emit frame sequential light.

The second rotation filter 26 rotates at a predetermined rotation speed about a rotation shaft of the second rotation filter 26 based on the control signal from the control unit 21, and continuously arranges the three filters of RGB in order on the light path of the emitted light of the lamp 23.

The condenser lens 27 is an optical device for condensing the illumination light transmitted through the two rotation filters (24 and 26) on a proximal end surface of the light guide 15.

The control unit 21 of the light source apparatus 3 selects the first rotation filter 24 to select the filter according to the observation mode switching switch 22a, and also controls the aperture apparatus 25 based on the signal related to the brightness from the video processor 4.

In addition, an operation signal from the front panel 22 of the light source apparatus 3 is inputted to a control unit 31, and the control unit 31 executes processing according to the function of the switch operated in the front panel 22.

A detailed configuration of the control unit 21 of the light source apparatus 3 will be described with reference to FIG. 4. As illustrated in FIG. 4, the control unit 21 is configured by various circuits mounted on a circuit board. The control unit 21 is constituted by various chips and circuits mounted on the board. The control unit 21 is configured by including a field programmable gate array (FPGA) 41, a lamp drive unit 42, filter drive units 43 and 44, an aperture drive unit 45, and the like.

The FPGA 41 includes a CPU 41a, a storage unit 41b including a ROM and a RAM, and an aperture control unit 41c.

The CPU 41a is configured by including an illumination mode switching control unit that switches, based on the signal from the observation mode switching switch 22a, the illumination mode corresponding to the normal light observation mode and the illumination mode corresponding to the special light observation mode.

The aperture control unit 41c is a control unit configured to output an aperture drive control signal according to a brightness target signal from the video processor 4. In other words, the aperture control unit 41c causes the aperture apparatus 25 serving as a light amount adjustment unit to execute an adjustment of the emitted light amount of the illumination light based on the brightness target signal corresponding to a light amount control signal generated based on the brightness of the image obtained by picking up the image of the subject.

The brightness target signal indicates a target value of the brightness, and the aperture control unit 41c controls the aperture apparatus 25, such that the target value indicated by the brightness target signal (abbreviated as a brightness target value) is set as a predetermined reference value.

More specifically, the aperture control unit 41c generates the aperture drive control signal for an instruction to close or an instruction to open the aperture apparatus 25 depending on whether the inputted brightness target value is higher or lower than the predetermined reference value, and outputs the aperture drive control signal to the aperture drive unit 45.

The lamp drive unit 42 outputs a lamp drive signal for turning on the lamp 23 serving as the light source based on a lamp drive control signal from the FPGA 41.

The filter drive unit 43 outputs a motor drive signal for driving a motor (not illustrated) that turns the first rotation filter 24 based on a filter drive control signal for controlling the first rotation filter 24 from the FPGA 41.

The filter drive unit 44 outputs the motor drive signal for driving a motor (not illustrated) that turns the second rotation filter 26 based on the filter drive control signal for controlling the second rotation filter 26 from the FPGA 41.

The aperture drive unit 45 outputs an aperture drive signal for driving the aperture apparatus 25 based on the aperture drive control signal for controlling the aperture apparatus 25 from the FPGA 41. A current aperture value based on a detection signal from a location detector such as a potentiometer disposed in the aperture apparatus 25 is fed back and inputted to the aperture drive unit 45, and the feedback signal is inputted to the aperture control unit 41c.

In this manner, the aperture drive unit 45 configured to drive the aperture apparatus 25 according to the aperture drive control signal inputted from the aperture control unit 41c constitutes the light amount adjustment unit with the aperture apparatus 25, the aperture control unit 41c, and the like.

Note that the light source apparatus 3 serving as the light source unit in the endoscope system 1 of the present embodiment is configured, as described above, in a manner that a xenon lamp that emits the white light serving as the normal light or the like is applied as a light source for supplying the illumination light to the subject, and when the white light transmits through the first rotation filter 24, the light source apparatus 3 selectively emits the light in the wavelength band for the normal light observation and the light in the wavelength band for the special light observation.

The configuration of the light source unit in the endoscope system 1 of the present invention is not limited to the above-described configuration, and other modes may also be adopted. As the configuration of the light source unit in other modes, for example, a mode is conceivable in which a plurality of light emitting diodes (LEDs) that may emit light at specific wavelengths are prepared, and light emissions of the plurality of light emitting diodes are appropriately switched according to the observation modes.

Next, the video processor 4 is a processing apparatus configured to control the entirety of the endoscope system 1 serving as the heat invasion observation apparatus of the present embodiment and also perform various kinds of data processing related to various kinds of information including the image data of the subject corresponding to the observation target obtained by the endoscope 2.

The video processor 4 is configured, as illustrated in FIG. 2, by mainly including the control unit 31, a light control unit 32, an image pickup drive unit 33, an image processing unit 34, a storage unit 35, an announcement unit 36, and the like.

The control unit 31 is a processing unit configured to control the entirety of the video processor 4 and is configured by including a central processing unit (CPU) or the like that controls the light control unit 32, the image pickup drive unit 33, the image processing unit 34, and the like according to the observation mode specified by the user.

The light control unit 32 generates a brightness target signal from luminance information (brightness information) of the image signal generated by the image processing unit 34 and displayed on the monitor 5, and supplies the brightness target signal to the control unit 21 of the light source apparatus 3. The brightness target signal is, for example, a signal indicating a value decided by calculation according to a comparison result between the brightness of the image signal displayed on the monitor 5 and the brightness set as a reference. In this manner, according to the present embodiment, the light control unit 32 functions as a surrounding light detection unit configured to detect the light amount in a surrounding of the distal end portion 11a of the insertion portion 11 of the endoscope 2 (surrounding of the subject set as the observation target) with the image pickup device 13, the image processing unit 34, and the like.

The image pickup drive unit 33 is a circuit configured to output an image pickup drive signal for driving the image pickup device 13 based on an image pickup drive control signal from the control unit 31.

The image processing unit 34 includes a function of receiving the image pickup signal from the image pickup device 13 under the control of the control unit 31, and executing various kinds of image signal processing on the image pickup signal. In addition, the image processing unit 34 includes a function of generating the display image data for displaying the image based on the above-described processed image signal on the monitor 5, and outputting the display image data to the monitor 5.

Specifically, the image processing unit 34 is configured by including a fluorescence image generation unit 34a, a white light image generation unit 34b, an information generation unit 34c, a display image generation unit 34d, a heat invasion depth calculation unit 34e, and the like.

The fluorescence image generation unit 34a is a circuit unit or program software configured to obtain the image pickup signal generated by picking up, by the image pickup device 13 of the endoscope 2, an image of the fluorescence generated from the heat invasion area of the subject irradiated with the exciting light from the light source apparatus 3, and generate fluorescence image data corresponding to the fluorescence based on the obtained image pickup signal.

The white light image generation unit 34b is a circuit unit or program software configured to generate the white light image data based on the image pickup signal obtained by the image pickup by the image pickup device 13 of the endoscope 2 when reflection light from the subject among the white light with which the subject is irradiated from the light source apparatus 3 (light source unit) is received.

The information generation unit 34c is a circuit unit or program software configured to calculate the fluorescence intensity information in a predetermined area (heat invasion area) in the fluorescence image represented by the fluorescence image data based on the fluorescence image data generated by the fluorescence image generation unit 34a.

In addition, the information generation unit 34c is a circuit unit or program software configured to further generate a fluorescence intensity information icon from the fluorescence intensity information calculated based on the fluorescence image data generated in the fluorescence image generation unit 34a.

Furthermore, the information generation unit 34c is a circuit unit or program software configured to generate heat invasion depth information based on the fluorescence intensity information calculated from the fluorescence image data generated in the fluorescence image generation unit 34a, and predetermined relationship information (detail will be described below) stored in the storage unit 35 in advance which will be described below.

Note that the above-described fluorescence intensity information is information including heat invasion range information representing the heat invasion area where the fluorescence intensity in the fluorescence image is equal to or higher than a predetermined intensity, heat invasion degree distribution information representing a distribution of fluorescence intensities on a subject surface in a range of the heat invasion area, heat invasion depth information from the subject surface in the range of the heat invasion area, and the like. The fluorescence intensity information is multiple pieces of information included in the fluorescence image data.

In addition, the above-described fluorescence intensity information icon is a signage in a symbolic mode by figures, characters, and the like in such a mode that, when the above-described fluorescence intensity information is displayed on the monitor 5, the information is clearly and also easily visually recognized for each type by a visual check.

The heat invasion depth information is information indicating a degree of depth of heat invasion in the heat invasion area. The heat invasion depth is information calculated based on data of the predetermined area (heat invasion area) of the fluorescence image data, and the predetermined relationship information (relationship information indicating a correlation relationship between the fluorescence intensity and the heat invasion depth of the fluorescence image).

The display image generation unit 34d is a circuit unit or program software configured to generate the display image data to be displayed on the monitor 5 (display unit) based on the white light image data and the fluorescence intensity information.

In addition, the display image generation unit 34d is a circuit unit or program software configured to generate the display image data to be displayed in a mode where the fluorescence intensity information is superimposed and emphasized on the image represented by the white light image data.

Further, the display image generation unit 34d is a circuit unit or program software configured to generate the display image data in a mode where the previously prepared fluorescence intensity information icon is superimposed on the image represented by the white light image data.

Furthermore, the display image generation unit 34d is a circuit unit or program software configured to generate the image data for superimposing and displaying the heat invasion depth information on the display image to be outputted to the display unit.

The heat invasion depth calculation unit 34e is a circuit unit or program software configured to calculate the heat invasion depth in the predetermined area (heat invasion area) in the image area represented by the fluorescence image data based on the fluorescence image data and the relationship information stored in the storage unit 35.

The storage unit 35 is a data storage as well as a storage apparatus that stores various information data, software programs, and the like in advance which are previously decided. The storage unit 35 stores, for example, information data or the like related to relationship information indicating a correlation relationship between the fluorescence intensity in the fluorescence image and the heat invasion depth at which the fluorescence intensity is generated in the biological tissue.

The announcement unit 36 is an announcement information generation unit configured to generate various messages (warnings, notices, and the like) appropriately issued during the use of the endoscope system 1 and announcement information such as use guide information like handling steps and support information.

The announcement information generated by the announcement unit 36 is outputted, for example, to an announcement device, and the announcement information is transmitted to the user. In this case, for example, a voice generation apparatus such as a speaker configured to output the announcement information as voice information in addition to the monitor 5 (display unit) that visually outputs (displays) the announcement information can also be applied as the announcement device.

Note that according to the present embodiment, when a value of the invasion depth of the heat invasion area which is calculated by the heat invasion depth calculation unit 34e reaches a predetermined depth or more, the announcement unit 36 is configured to generate the corresponding announcement information, and output the corresponding announcement information to the monitor 5 (display unit), so that the announcement information is displayed in a predetermined area on a display screen of the monitor 5.

Note that the above-described announcement information is mainly generated in the announcement unit 36. As a different mode from the above-described mode, for example, a configuration may also be adopted where the above-described announcement information is generated in the information generation unit 34c, the heat invasion depth calculation unit 34e, or the like based on the heat invasion depth calculated by the heat invasion depth calculation unit 34e.

The monitor 5 is a display unit corresponding to a display device configured to display various kinds of information in a predetermined mode that may be visually checked including, in addition to images based on various image data such as the fluorescence image data and the white light image data and various kinds of information and the like associated with the display image, various kinds of setting information and the like related to the endoscope system 1, and also various kinds of information (such as patient medical record information) related to the subject of the observation target.

A trolley 6 is configured, as illustrated in FIG. 1, by including a trolley main body 50, and a trestle apparatus 51 for endoscope installed side by side with the trolley main body 50.

The trolley main body 50 includes a frame 55 substantially forming an inverted U shape in a front view. A plurality of shelves 56 are erected in the frame 55. For example, the light source apparatus 3 and the video processor 4 are placed on top of each other on one of the plurality of shelves 56. Note that the illustration is omitted, but a group of various other devices configuring the endoscope system 1 are placed on the respective shelves 56 as necessary.

In addition, wheels 57 are disposed on a back side of the shelf 56 located in a lowest stand, such that the trolley 6 may be moved on a floor.

Furthermore, a display unit mounting arm 58 is fixed and disposed in a top part of the frame 55, and the display unit 5 is mounted on a free end side of the display unit mounting arm 58.

The trestle apparatus 51 for endoscope is configured by including a brace 60, a brace support portion 61 for supporting a proximal end side (lower end side) of the brace 60, two hangers 62 disposed, for example, on a distal end side (upper end side) of the brace, and the like.

The brace 60 is configured is by a rod-like member in a manner that a middle part is bent, and a predetermined section on the distal end side is formed to extend in a horizontal direction. A hanger support portion 60a is formed in a section extending in the horizontal direction of the brace 60.

The brace support portion 61 is fixed and disposed in one side portion of the frame 55 (for example, a right side of the frame 55 in the illustrated example). The brace support portion 61 is formed to have a pipe shape in which an upper end is opened, and the proximal end side of the brace 60 may be inserted into an inside of the brace support portion 61. In addition, for example, a knurling screw type support fixing portion 61a is disposed in the upper end part of the brace support portion 61, so that the proximal end side of the brace 60 inserted into the inside of the brace support portion 61 is fixed at any height. The other configurations that are not described are substantially similar to the conventional configurations of the widely available endoscope system.

An action performed by using the thus configured endoscope system 1 of the present embodiment will be described below.

When a minimally invasive surgery is performed by using the endoscope system 1 of the present embodiment, first, marking for specifying a location of a lesion portion set as a surgery target is performed.

For example, to implement a procedure based on an endoscopic submucosal dissection (ESD), the following processes are conducted:

(1: Check) a lesion portion (biological tissue) is checked under endoscope observation, (2: Marking) marking is performed through cautery by applying heat energy to a surrounding of the lesion portion by using a treatment instrument like an energy device or the like such as an electric scalpel inserted to the treatment instrument insertion channel of the endoscope, (3: Local injection) normal saline or the like is injected under the mucosa of the lesion portion by using another treatment instrument (injection needle for endoscope), (4: Dissection) the mucosa surrounding the marking is dissected by using an energy device such as an electric scalpel or a treatment instrument such as a high frequency knife again, (5: Submucosal layer detachment) the lesion portion is detached by using the same treatment instrument, (6: Resection) finally, the lesion portion is resected by using a treatment instrument such as a snare, and (7: Hemostasis) hemostasis treatment is applied to the surface after the lesion portion is resected, and the cut lesion portion is collected.

Note that a tissue examination or the like by a microscope is performed on the collected lesion portion.

In this case, the heat invasion by the cautery is applied in the marking step illustrated in the above-described (2) and the dissection step illustrated in the above-described (4).

When amino acid and sugar are heated at the same time, a glycation reaction (Maillard reaction) is caused. It is known that end products called advanced glycation end products (AGEs) are produced by the Maillard reaction.

In other words, the cautery treatment is applied to the biological tissue or the like by the energy device or the like, amino acid and reduction sugar in the biological tissue are heated to cause Maillard reaction, and as a result, AGEs are produced. It is found that as a characteristic of the AGEs, a substance having a fluorescence property is included.

In view of the above, in the endoscope system of the present embodiment, fluorescence emitted from the AGEs present in the heat invasion area is observed.

Note that the AGEs are produced in the heat invasion area by the heating as described above, but in addition, it is found that the AGEs are present in a human body, and an association with aging or disease is pointed out.

For example, it is said that the AGEs are also contained in an aged substance, a cancer tissue, or the like. In addition, it is said that the AGEs affect aging of the biological tissue, wrinkle, fleck, cancer, osteoporosis, Alzheimer's disease, cataract, arterial sclerosis, diabetes, or the like. In view of the above, a technology for visually detecting the AGEs is useful in the medical field.

In addition, it is found that substances produced by the heat processing (AGEs) emit more intense fluorescence than autofluorescence substances originally present in the biological tissue.

In a case where the endoscope system 1 of the present embodiment is used, at the time of the steps (2) and (4), the special light observation (fluorescence observation) is performed.

In this case, for example, in a case where irradiation with at least the exciting light at wavelengths of 300 to 400 nm is performed, when fluorescence at wavelengths of 400 to 590 nm is observed (image pickup), the heat invasion area can be visualized. In addition, in a case where irradiation with at least the exciting light at wavelengths of 400 to 480 nm is performed, when fluorescence at wavelengths of 510 to 600 nm is observed (image pickup), the heat invasion area can be visualized.

Figure 10:
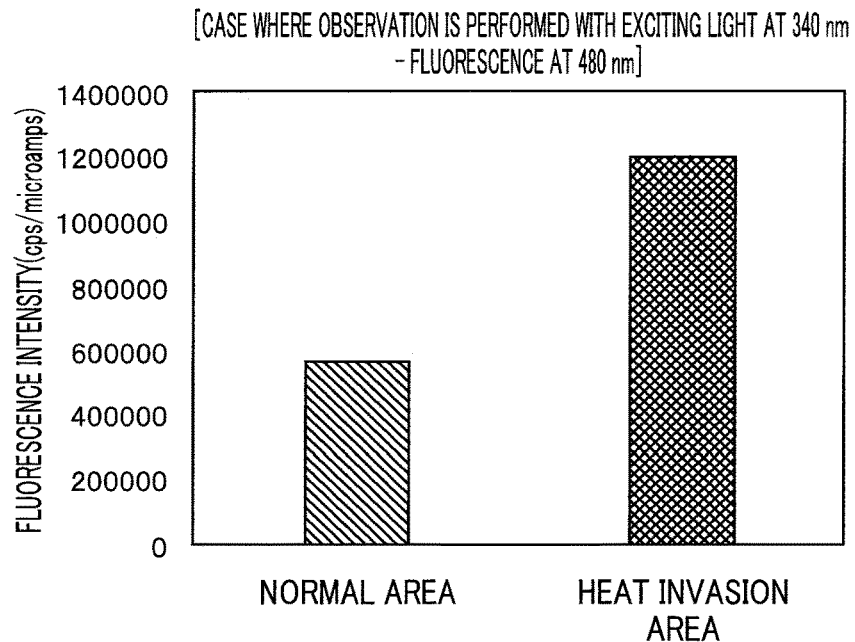
FIG. 10 is a diagram in which a fluorescence intensity on a biological tissue is graphed in a case where a fluorescence observation at a wavelength of 480 nm is performed by irradiation with exciting light at a wavelength of 340 nm (case of a wavelength suitable to visualize a heat invasion area)

More specifically, for example, FIG. 10 is a diagram in which the fluorescence intensity on the biological tissue is graphed in a case where the fluorescence observation at a wavelength of 480 nm is performed by the irradiation with the exciting light at a wavelength of 340 nm.

Figure 11:
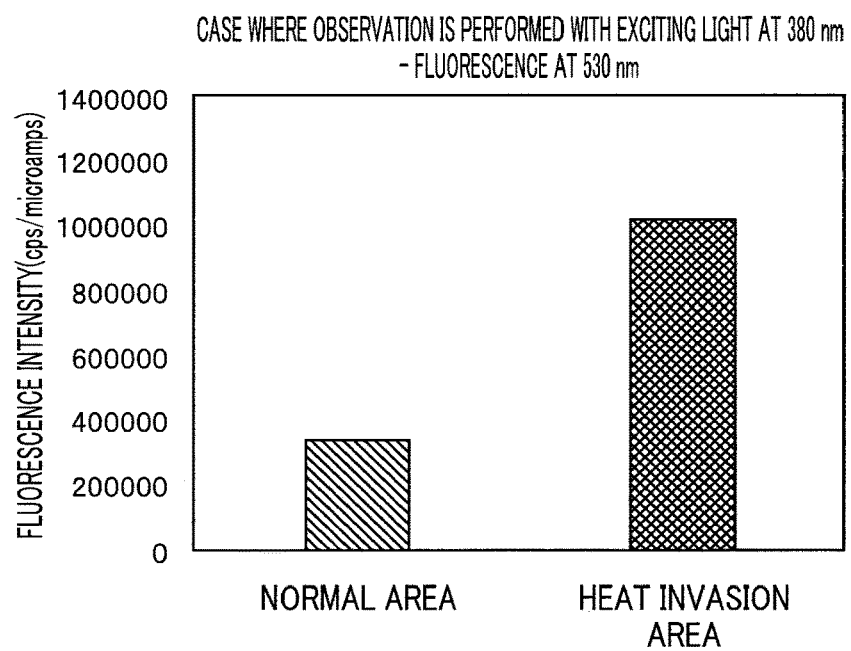
FIG. 11 is a diagram in which the fluorescence intensity on the biological tissue is graphed in a case where the fluorescence observation at a wavelength of 530 nm is performed by the irradiation with the exciting light at a wavelength of 380 nm (case of a wavelength suitable to visualize the heat invasion area)

FIG. 11 is a diagram in which the fluorescence intensity on the biological tissue is graphed in a case where the fluorescence observation at a wavelength of 530 nm is performed by the irradiation with the exciting light at a wavelength of 380 nm.

Figure 12:
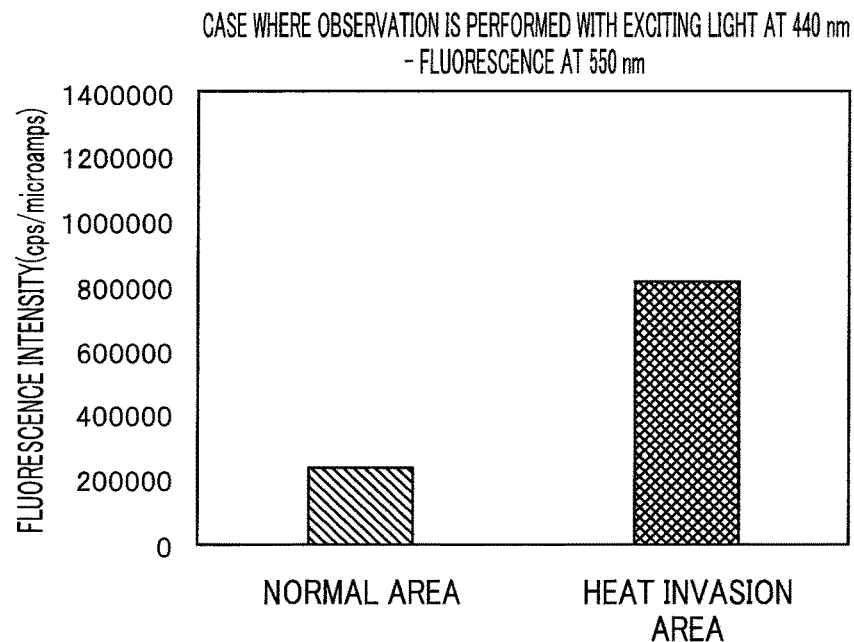
FIG. 12 is a diagram in which the fluorescence intensity on the biological tissue is graphed in a case where the fluorescence observation at a wavelength of 550 nm is performed by the irradiation with the exciting light at a wavelength of 440 nm (case of a wavelength suitable to visualize the heat invasion area)

FIG. 12 is a diagram in which the fluorescence intensity on the biological tissue is graphed in a case where the fluorescence observation at a wavelength of 550 nm is performed by the irradiation with the exciting light at a wavelength of 440 nm.

The respective examples illustrated in FIG. 10 to FIG. 12 illustrate cases where wavelengths of the exciting light (300 to 400 nm) and fluorescence (400 to 590 nm) that are suitable for visualizing the heat invasion area are selected. In this case, since the difference of the fluorescence intensities is large in any one of the exemplifications in FIG. 10 to FIG. 12, the heat invasion area can be clearly displayed as the image.

Figure 13:
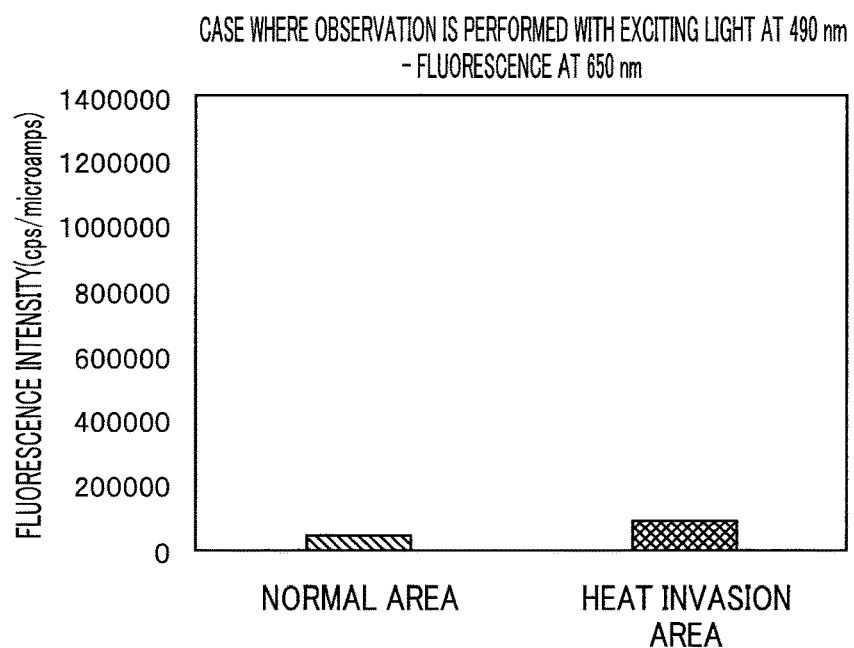
FIG. 13 is a diagram in which the fluorescence intensity on the biological tissue is graphed in a case where the fluorescence observation at a wavelength of 650 nm is performed by the irradiation with the exciting light at a wavelength of 490 nm (case of a wavelength that is not suitable to visualize the heat invasion area)

FIG. 13 is a diagram in which the fluorescence intensity on the biological tissue is graphed in a case where the fluorescence observation at a wavelength of 650 nm is performed by the irradiation with the exciting light at a wavelength of 490 nm. In addition, FIG. 14 is a diagram in which the fluorescence intensity on the biological tissue is graphed in a case where the fluorescence observation at a wavelength of 430 nm is performed by the irradiation with the exciting light at a wavelength of 410 nm.

Figure 14:
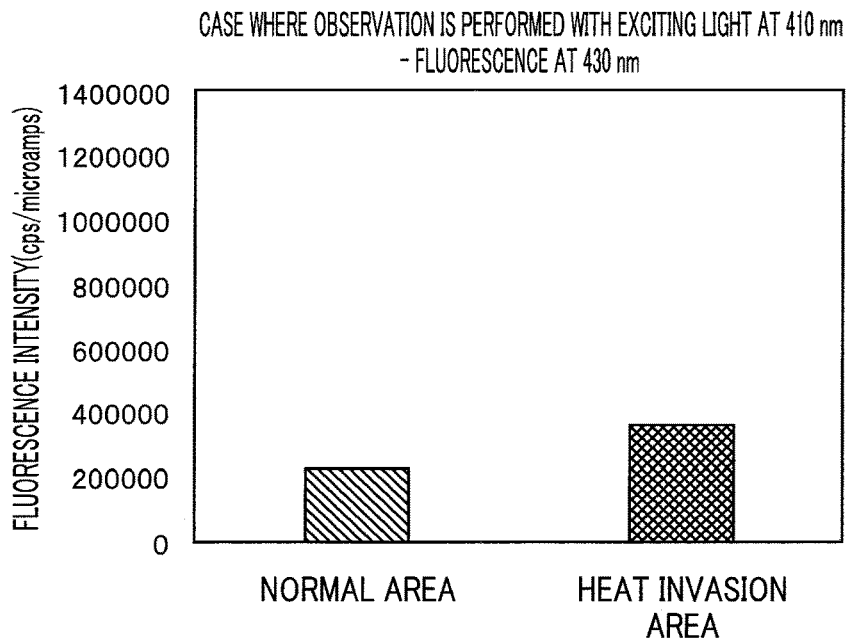
FIG. 14 is a diagram in which the fluorescence intensity on the biological tissue is graphed in a case where the fluorescence observation at a wavelength of 430 nm is performed by the irradiation with the exciting light at a wavelength of 410 nm (case of a wavelength that is not suitable to visualize the heat invasion area)

The examples illustrated in FIG. 13 and FIG. 14 illustrate cases where the exciting light at wavelengths (490 nm, 410 nm) and fluorescence at wavelengths (650 nm, 430 nm) which are not suitable to visualize the heat invasion area are selected. In this case, in any of the exemplifications in FIG. 13 and FIG. 14, since the difference of the fluorescence intensities is small, it is difficult to clearly display the heat invasion area as the image.

When the fluorescence observation is performed on the subject including the area applied with the heat invasion, the area applied with the heat invasion generates fluorescence by receiving the exciting light from the light source apparatus 3. When an image of the fluorescence is picked up by the image pickup device 13 of the endoscope 2, the predetermined image processing is applied to an image pickup signal obtained by the image pickup device 13 by the fluorescence image generation unit 34a of the image processing unit 34, and the fluorescence image data is generated.

After the thus generated fluorescence image data is applied with predetermined data processing in the image processing unit 34 and converted into the image data in a display mode, the fluorescence image data is outputted to the monitor 5. The monitor 5 displays the fluorescence image according to the fluorescence image data and various kinds of information associated with the fluorescence image.

At this time, the fluorescence image displayed on the monitor 5 is visualized in a state where the area applied with the heat invasion (marking area) is clear against the surrounding area. For the display at this time, heat invasion range information among the fluorescence intensity information included in the fluorescence image data is mainly used.

In addition, for example, when a procedure based on a laparoscopy and endoscopy cooperative surgery (LECS) is implemented, first, the steps (1) to (4) are similarly performed as in the ESD procedure described above.

In the conventional LECS procedure, at this time,
(5: Perforation) after the lesion portion dissection, perforation is performed by a spicule scalpel under the endoscope, and
(6: Full thickness cutoff) an energy device is inserted from a perforated portion under a laparoscope, and full thickness cutoff is performed along a surrounding dissection line of the ESD. At this time, since it is difficult to check whether or not the energy device is on the surrounding dissection line of the ESD from an outer side (serous membrane side), the check is performed under the endoscope.
(7: Suture) a gastric wall deficit portion is closed by using an automatic suture device under the endoscope.

However, in the endoscope system 1 of the present embodiment, the marking area by the heat invasion to the inner side (mucosa side) which is applied in the marking step in the above-described (2) can also be checked from the outer side by the fluorescence observation under the laparoscope.

Therefore, in the full thickness cutoff step in the above-described (6), whether or not the energy device is on the surrounding dissection line of the ESD can be checked from the outer side (serous membrane side) by performing the fluorescence observation under the laparoscope without the reliance of the endoscope. In other words, in the full thickness cutoff step in the above-described (6), the procedure can be implemented by the laparoscope alone. Therefore, it is possible to avoid the check under the endoscope.

Furthermore, for example, when the procedure by a non-exposed endoscopic wall-inversion surgery (NEWS) is implemented, first, the steps (1) and (2) are performed similarly as in the ESD procedure described above.

In the conventional NEWS procedure, at this time,
(3: Second marking) marking is performed from the outer side (serous membrane side) under the laparoscope,
(4: Lesion resection) local injection is performed in the submucosal layer, and the serous membrane muscle layer is resected under the laparoscope,
(5: Suture) the lesion portion is pressed from the outer side towards a lumen side (inner side) and sutured under the laparoscope, and
(6: Lesion resection) the full thickness lesion portion is resected from the inner side under the endoscope.

However, in the endoscope system 1 of the present embodiment, the marking area by the heat invasion to the inner side (mucosa side) which is applied in the marking step in the above-described (2) can also be checked from the outer side by the fluorescence observation under the laparoscope.

Therefore, the second marking step in the above-described (3) can be skipped.

In this manner, with the endoscope system 1 of the present embodiment, since the fluorescence observation is performed on the marking area by the heat invasion, the observation can be clearly and also easily performed from the outer side of the subject (biological tissue) set as the target. Therefore, a part of internal and external cooperative operations performed in the conventional procedure, the special marking method, and the like can be skipped, which contributes to the simplification of the procedure.

The explanation of the embodiment described above illustrates an example of a case where the fluorescence image based on the fluorescence image data obtained by performing the fluorescence observation is directly displayed on the monitor 5 to facilitate the check on the marking area by the heat invasion by a visual check. In a first modification described next, with the application of the predetermined image processing based on the fluorescence image data, the marking area by the heat invasion can be further clearly checked.

Figure 5:
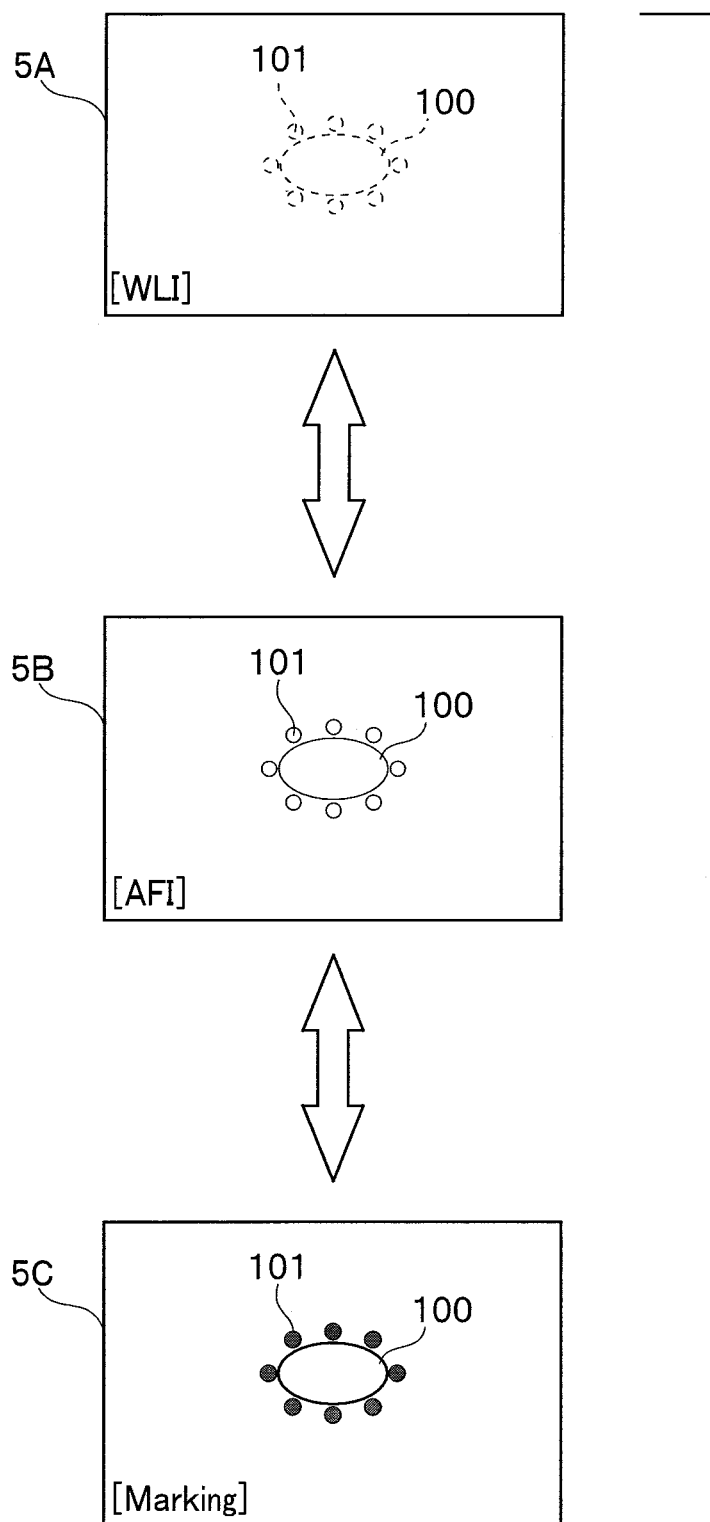
FIG. 5 is a diagram illustrating a first modification with regard to display of a marking area by a heat invasion in the endoscope system of one embodiment of the present invention.

FIG. 5 is a diagram illustrating the first modification with regard to display of the marking area by the heat invasion in the endoscope system of one embodiment of the present invention.

In FIG. 5, frames denoted by reference signs 5A, 5B, and 5C are display frames of the monitor 5. Each of the display frames 5A, 5B, and 5C illustrates a state in which a lesion portion 100 set as an observation target and a marking area (heat invasion area) 101 added around the lesion portion 100 are displayed.

Herein, the display frame 5A schematically illustrates a display state of the target lesion portion 100 and the marking area (heat invasion area) 101 surrounding the target lesion portion 100 when the normal white light observation (WLI) is performed. The setting at this time is referred to as the white light observation mode (or the normal light observation mode).

In the white light observation mode (the display frame 5A of FIG. 5), a situation is illustrated where the lesion portion 100, the marking area 101 surrounding the lesion portion 100, and further the normal tissue surrounding the lesion portion 100 and the marking area 101 are not clearly displayed, and therefore, the lesion portion 100 and the marking area 101 are easily overlooked.

The display frame 5B schematically illustrates a display state of the target lesion portion 100 and the marking area (heat invasion area) 101 surrounding the target lesion portion 100 when the fluorescence observation is performed. The setting at this time is referred to as the fluorescence observation mode.

In the fluorescence observation mode (the display frame 5B of FIG. 5), a situation is illustrated where the lesion portion 100 and the marking area 101 surrounding the lesion portion 100 are clearly displayed against the normal tissues surrounding the lesion portion 100 and the marking area 101, and the lesion portion 100 and the marking area 101 are easily identified.

The present modification includes the marking check mode in which the marking area 101 surrounding the lesion portion 100 is displayed in a mode to further facilitate the identification, and the check can be easily performed. The display frame 5C of FIG. 5 illustrates an example of the display at this time.

Herein, in the marking check mode, the display image data to be displayed on the monitor 5 (display unit) is generated based on the white light image data and the fluorescence image data obtained when the white light observation (WLI) and the fluorescence observation are performed at the same time.

Specifically, extraction emphasis data is generated in a manner that only image data of an area corresponding to the marking area (heat invasion area) 101 surrounding the target lesion portion 100 is extracted from the fluorescence image data, and the image processing such as predetermined emphasis processing (for example, contour emphasis or coloring processing in the relevant area) is applied to the extracted data. Then, processing for superimposing and displaying the extraction emphasis data on the corresponding area in the white light image data is performed. The image displayed when the thus obtained display image data is outputted to the monitor 5 is the display frame 5C of FIG. 5.

In other words, the display frame 5C schematically illustrates a display state of the target lesion portion 100 and the marking area (heat invasion area) 101 surrounding the target lesion portion 100 when the marking check mode is set to observe the area including the target lesion portion 100.

In the marking check mode (the display frame 5C of FIG. 5), a situation is illustrated where the marking area 101 surrounding the lesion portion 100 is more clearly displayed against the lesion portion 100 and the surrounding normal tissues, and the marking area 101 is further easily identified.

In this manner, since the marking check mode in which the image processing for further emphasizing and displaying the marking area 101 is applied is provided, the location of the lesion portion 100 surrounded by the marking area 101 can be certainly figured out, and it is possible to prevent overlooking of the lesion portion 100.

When the marking check mode is set, the complication for performing the switch to another observation mode is eliminated, and the heat invasion area can be clearly displayed, while the observation, the treatment, and the like are performed all the time under the normal white light.

Note that a configuration is adopted where the white light observation mode, the fluorescence observation mode, and the marking check mode can be optionally switched by appropriately operating the observation mode switching switch 22a of the front panel 22 by the user at a desired time.

In addition, according to the present embodiment, the example is illustrated in which the observation mode switching switch 22a is disposed on the front panel 22 of the light source apparatus 3, but the arrangement of the observation mode switching switch 22a is not limited to this arrangement.

For example, the observation mode switching switch 22a may also be disposed on a surface of the operation portion 12 of the endoscope 2. With such a configuration, the user can appropriately switch the observation modes at a desired timing while the endoscope 2 is operated, so that the configuration is convenient.

Note that a configuration may also be adopted where the observation mode switching switch 22a may be disposed on each of the front panel 22 of the light source apparatus 3 and the operation portion 12.

Note that the display example at the time of the marking mode in the present modification (the display frame 5C of FIG. 5) illustrates an example in which by using the extraction emphasis data generated by extracting the image data of the area corresponding to the marking area (heat invasion area) 101, the marking is superimposed and displayed on the corresponding area of the white light image data, but the following mode may also be adopted as a display mode different from the above-described mode.

For example, the fluorescence intensity information icon is generated by iconifying the generated extraction emphasis data, and the fluorescence intensity information icon is superimposed and displayed on the corresponding area of the white light image data. In this case, the data can be reduced by the iconifying processing. Therefore, the iconifying processing contributes to the reduction of a capacity of the display image data, and may realize an increase in a display speed.

The explanation thus far illustrates the configuration example particularly focused with regard to the display of the marking area by the heat invasion. The heat invasion range information among the fluorescence intensity information included in the fluorescence image data is mainly used as the information used in this case.

The fluorescence image data obtained by the endoscope system 1 serving as the heat invasion observation apparatus of the present embodiment includes still more information. Each of modifications described below indicates a display example in a case where other information such as the heat invasion degree distribution information and the heat invasion depth information among the fluorescence intensity information included in the fluorescence image data is used.

Figure 6:
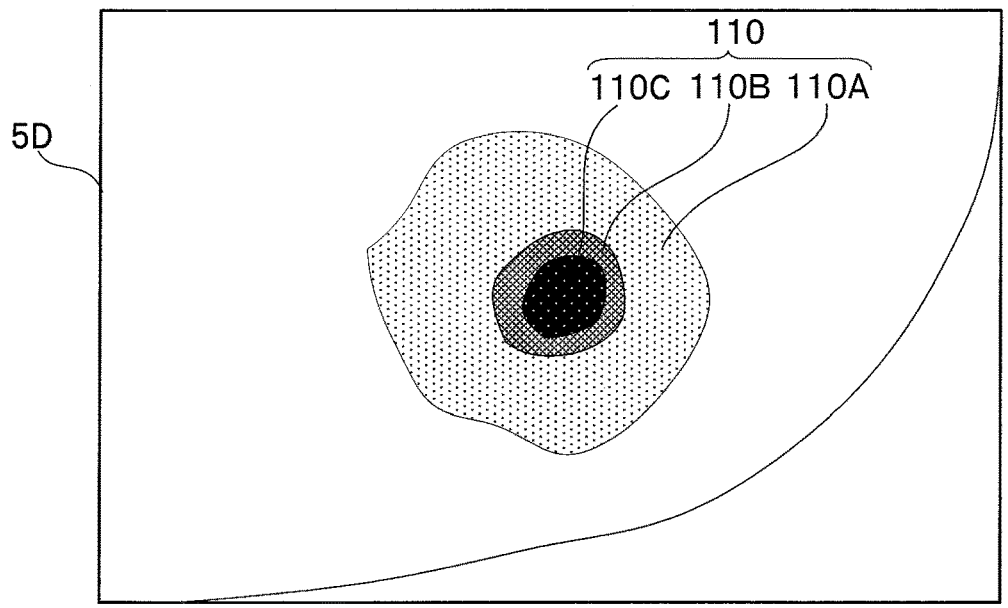
FIG. 6 is a diagram illustrating a second modification with regard to a display example when cautery based on the heat invasion to a subject is performed by using the endoscope system of the present embodiment, and the subject including an area of the cautery is observed in a fluorescence observation mode.
Figure 7:
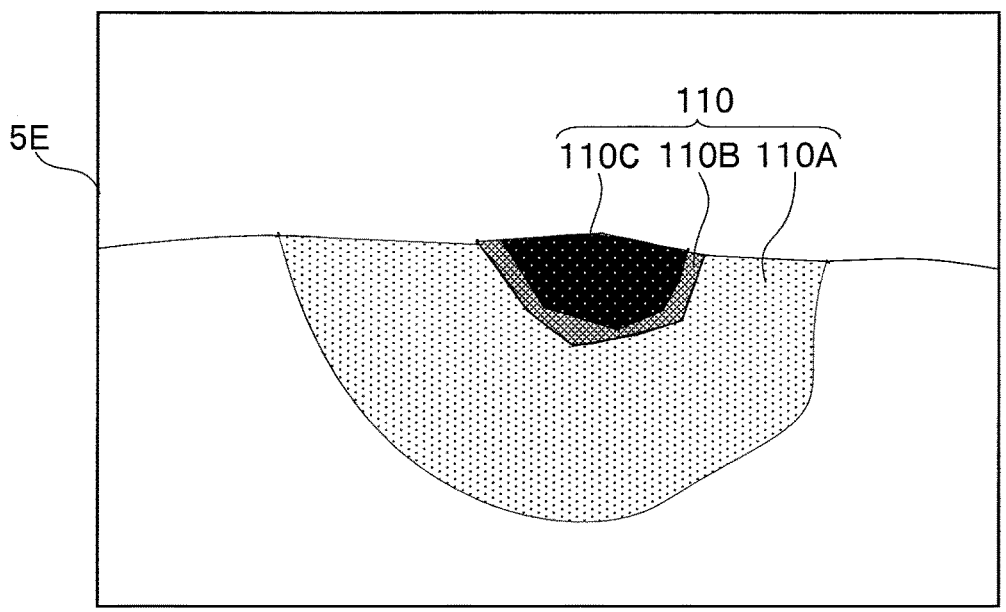
FIG. 7 is a diagram illustrating a display example in which a depth of the heat invasion is displayed which is estimated from a result calculated by using heat invasion depth information among fluorescence intensity information included in fluorescence image data of FIG. 6.

FIG. 6 illustrates a second modification with regard to a display example when the cautery based on the heat invasion to the subject is performed by using the endoscope system 1 of the present embodiment, and the subject including the cautery area is observed in the fluorescence observation mode. FIG. 7 is a display example in which the depth of the heat invasion is displayed which is estimated from the result calculated by using the heat invasion depth information among the fluorescence intensity information included in the fluorescence image data of FIG. 6.

As described above, the fluorescence image data obtained by performing the fluorescence observation of the cautery area where the cautery by the heat invasion is performed by using the endoscope system 1 of the present embodiment includes the heat invasion degree distribution information and the heat invasion depth information.

In view of the above, the display example in the second modification realizes the display mode (see the display frame 5D of FIG. 6) in which the distribution of the fluorescence intensities in the range of the heat invasion area is displayed by using the heat invasion degree distribution information.

In the display example illustrated in FIG. 6, the distribution of the fluorescence intensities is classified into a plurality of areas (reference signs 110A, 110B, and 110C of FIG. 6) in a range of a cautery area (heat invasion area) 110 by the heat invasion to be displayed in different modes (for example, gray level display). According to this, the distribution of the fluorescence intensities on the subject surface in the range of the heat invasion area can be displayed in a state where the distribution may be visually checked.

Furthermore, a positive correlation relationship is recognized between the fluorescence intensity and the heat invasion depth, and in the endoscope system 1 of the present embodiment, the relationship information representing the correlation relationship between the fluorescence intensity and the heat invasion depth is stored in the storage unit 35.

Figure 15:
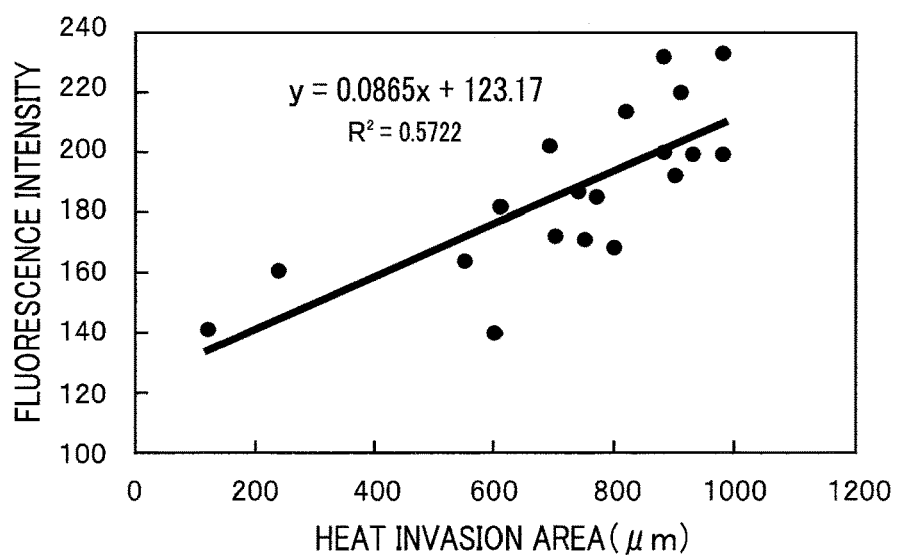
FIG. 15 is a diagram illustrating a correlation relationship between a heat invasion depth and the fluorescence intensity when the fluorescence observation of the heat invasion area is carried out by performing irradiation with the exciting light at wavelengths of 390 nm to 470 nm and picking up an image of fluorescence at 500 nm to 640 nm.

For example, FIG. 15 is a diagram illustrating the correlation relationship between the fluorescence intensity and the heat invasion depth. In FIG. 15, a vertical axis represents the fluorescence intensity. At this time, the fluorescence intensity represents a luminance value (0 to 255) of a pixel of the obtained fluorescence image (no unit). When an image of fluorescence at 500 nm to 640 nm is picked up by irradiation with the exciting light at wavelengths of 390 nm to 470 nm, the positive correlation relationship as illustrated in FIG. 15 is seen between the heat invasion depth and the fluorescence intensity when the fluorescence observation in the heat invasion area is performed.

In view of the above, in the endoscope system 1 of the present embodiment, the heat invasion depth calculation unit 34e calculates the heat invasion depth based on the relationship information in the storage unit 35 and the heat invasion depth information of the heat invasion area included in the fluorescence image data which is obtained by the fluorescence observation. When the thus obtained heat invasion depth result is used, the display mode as illustrated in FIG. 7, that is, the display of the estimated depth according to the distribution of the fluorescence intensities (110A, 110B, and 110C) of the cautery area by the heat invasion (heat invasion area) 110 is performed (see the display frame 5E of FIG. 7).

The display example illustrated in FIG. 7 shows that the invasion depth varies according to the fluorescence intensity distribution illustrated in FIG. 6. At this time, reference signs 110A, 110B, and 110C respectively correspond to reference signs 110A, 110B, and 110C denoting the distribution areas illustrated in FIG. 6.

Figure 8:
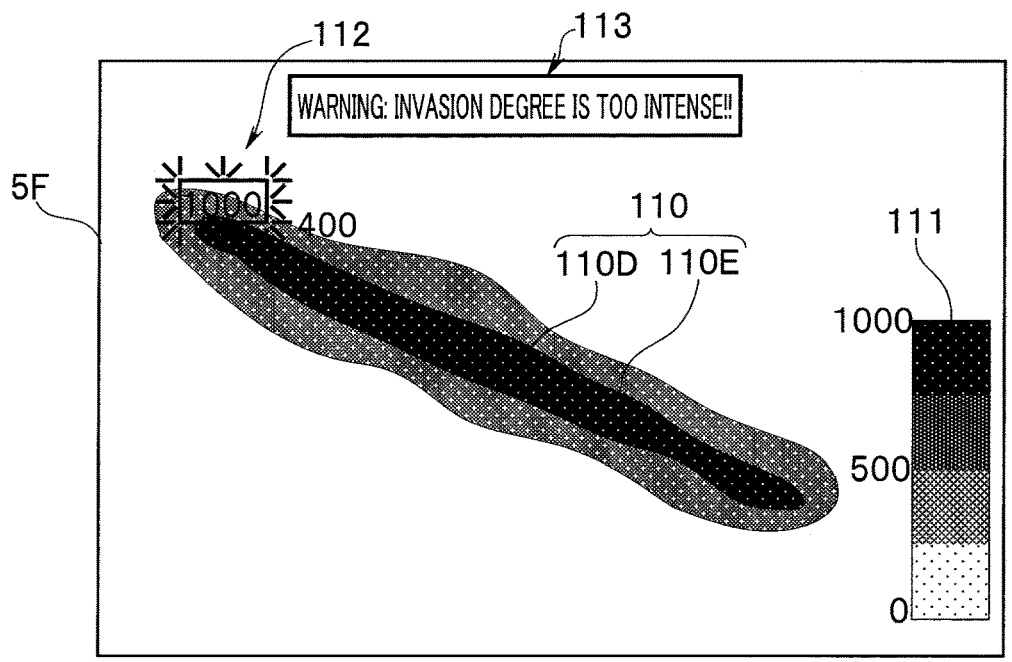
FIG. 8 is a diagram illustrating one example of a third modification with regard to a display example when the cautery based on the heat invasion to the subject is performed by using the endoscope system of one embodiment of the present invention, and the subject including the cautery area is observed in the fluorescence observation mode.
Figure 9:
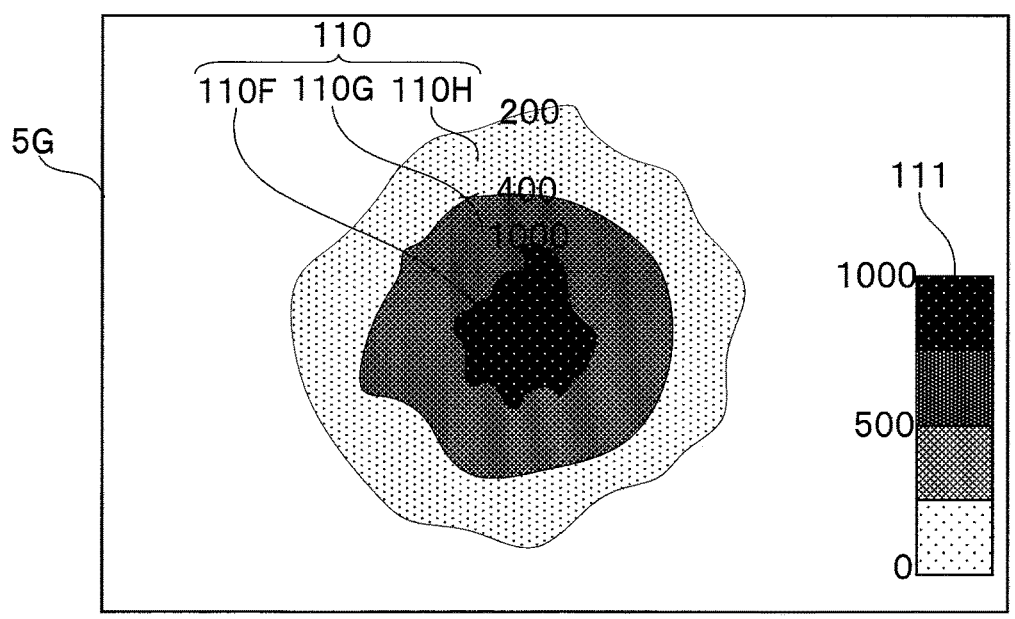
FIG. 9 is a diagram illustrating another example of the third modification of the display example in the endoscope system of one embodiment of the present invention.

In addition, FIG. 8 and FIG. 9 illustrate a third modification with regard to the display example when the cautery based on the heat invasion to the subject is performed by using the endoscope system 1 of the present embodiment, and the subject including the cautery area is observed in the fluorescence observation mode. The display example illustrated in FIG. 8 and FIG. 9 is a display example in which the depth of the heat invasion is displayed which is estimated from the result calculated by using the heat invasion degree distribution information and the heat invasion depth information among the fluorescence intensity information included in the fluorescence image data.

In the example illustrated in FIG. 8, the cautery area by the heat invasion which is formed into substantially an elongated shape on the surface of the subject is set as the target area. In this case, reference signs 110D and 110E of FIG. 8 denote the heat invasion degree distribution. Then, in FIG. 8, a number represented in the vicinity of the cautery area (heat invasion area) 110 in a display frame 5F of the monitor 5 is a display of specific information of the depth of the heat invasion calculated according to the distribution information.

Note that a graph 111 representing an indication of gray level information representing the distribution of the fluorescence intensities is configured to be displayed to match with a predetermined area in the display area in the display frame 5F (in the example illustrated in FIG. 8, an area closer to a lower edge on the right side facing the display frame 5F).

Similarly, in the display example illustrated in FIG. 9, the cautery area 110 by the heat invasion which is formed into substantially a circular shape on the surface of the subject is set as the target area. In this case, reference signs 110F, 110G, and 110H of FIG. 9 denote the heat invasion degree distributions. Then, in FIG. 9, an aspect that specific information of the depth of the heat invasion calculated according to the distribution information is displayed using a number in the vicinity of the cautery area (heat invasion area) 110 in a display frame 5G of the monitor 5 is the same as the display example of FIG. 8. Furthermore, the graph 111 is also similar to the graph of FIG. 8.

In this manner, when the cautery area by the heat invasion is displayed in the display modes as illustrated in FIG. 6 to FIG. 9, the cautery range (distribution) and the invasion range (invasion depth) can be clarified and displayed.

Therefore, for example, when the user performs the procedure for performing the cautery by the heat invasion under the endoscope, the procedure is performed while the endoscope image displayed on the monitor 5 is observed with regard to an area set as a target of the cautery (area including the target lesion portion or the like).

At this time, in the endoscope system 1 of the present embodiment, the white light observation and the fluorescence observation are performed at the same time to obtain the white light image data and the fluorescence image data at the same time, and when the predetermined image signal processing is applied by using the fluorescence intensity information included in the fluorescence image data (among the information, in particular, the heat invasion degree distribution information and the heat invasion depth information), the display image in a mode in which the cautery range (distribution) and the invasion range (invasion depth) are clarified can be observed in real time.

Therefore, the operator such as the doctor (user) can perform the procedure while checking the invasion degree of the area set as the target all the time. At the same time, for example, during a course in which the procedure is implemented by using the energy device in a body cavity of the subject, it is possible to prevent an accident where the heat invasion by the energy device is unintentionally caused to the normal area other than the target area.

Furthermore, even when the unintended heat invasion by the energy device is performed on the normal area, since a degree of the unintended heat invasion to the area can be checked in real time, it is possible to immediately promptly implement remedy treatment or the like as necessary. Therefore, it is possible to prevent development of complications or the like after the surgery which is conventionally worrying beforehand.

Furthermore, in the endoscope system 1 of the present embodiment, when the procedure accompanying the cautery by the heat invasion is performed, as described above, the heat invasion depth calculation unit 34e calculates the heat invasion depth.

In view of the above, for example, during the surgery, when the heat invasion depth calculated by the heat invasion depth calculation unit 34e reaches a predetermined depth that is previously set or higher or reaches a depth approximate to the predetermined depth that is previously set, the announcement unit 36 configured to announce the announcement information to that effect is included.

In the endoscope system 1 of the present embodiment, as described above, the announcement unit 36 outputs the generated announcement information to the monitor 5, and the generated announcement information is displayed as the visual announcement information on the display screen of the monitor 5 (display unit). In the display example, for example, together with display of the indicator as denoted by reference sign 112 illustrated in FIG. 8, a warning in the mode as denoted by reference sign 113 of the same FIG. 8 may be displayed (display of character information or a pictogram), and also a previously prepared warning icon stored in the storage unit 35 may also be appropriately read and displayed.

Note that with regard to the warning display in the example illustrated in FIG. 8, a further display representation is conceivable in which coloring display is performed by setting a text color in red, or flashing display is performed, such that it is facilitated to further call attention of the operator.

In addition, although an illustration in the drawing is omitted as a different mode from the above-described mode, a voice generation apparatus such as a speaker that outputs the announcement information as the voice information may also be applied as the announcement unit 36.

In a case where a desired area of the subject is observed in the fluorescence observation mode by using the endoscope system 1 of the present embodiment, autofluorescence may also be emitted in an area where the heat invasion is absent. By taking into account the phenomenon, the following display can also be performed in the endoscope system 1 of the present embodiment.

As described above, in the endoscope system 1 of the present embodiment, for example, the white light image data and the fluorescence image data can be obtained at the same time by performing the white light observation and the fluorescence observation at the same time.

Therefore, in a case where the cautery by the heat invasion is performed in the desired area while a target area of the subject is observed by using the endoscope system 1, the fluorescence image data before the treatment by the energy device, that is, the heat invasion is applied to the predetermined area, and the fluorescence image data after the treatment are obtained.

In view of the above, difference data is obtained by applying the predetermined image processing based on the fluorescence image data before and after the treatment. It can be said that the difference data is data accurately representing an intensity difference of the autofluorescence before and after the heat invasion treatment by the energy device in a mode where noise is removed.

In addition, as means different from the above-described means, for example, in a case where the cautery by the heat invasion is performed on a desired area in a target organ, means for obtaining difference data between the fluorescence image data of the "burnt area" and the fluorescence image data of an '(unburnt) area that is adjacent to the "burnt area" and does not receive the burn' is also conceivable.

According to this means, unlike the above-described means, that is, the image difference data in different time-series before and after the treatment, the difference of the image data in the same organ and also in equivalent time series is obtained.

In general, since characteristics of the autofluorescence vary for each organ, when a "burnt area" and 'the area that is adjacent to the "burnt area" and does not receive the burn' are the same organ, the difference data obtained from the image data can be represented by a more accurate and clearer image.

Therefore, when the display image data is generated based on the difference data, and the display image data is outputted to the monitor 5, only the area of the autofluorescence generated by the heat invasion can be clearly and also accurately displayed on the monitor 5.

As described above, with the endoscope system 1 serving as the heat invasion observation apparatus of the present embodiment, the range (the distribution or the depth) of the cautery area by the heat invasion on the biological tissue by using the energy device can be easily visualized by detecting the autofluorescence of the biological tissue.

In addition, since various kinds of image signal processing are performed by focusing on the recognition of the correlation relationship between the heat invasion depth and the fluorescence intensity, the operator such as the doctor (user) can check the range of the cautery area by the heat invasion in real time. Therefore, when the endoscope system 1 of the present embodiment is used, the reliable and highly precise minimally invasive surgery can be easily implemented all the time. Note that, in this case, as the check on the range or the degree of the cautery area at the time of the marking or the procedure by the heat invasion, the check can also be performed in a range (depth distribution) in a depth direction in addition to the range (surface distribution) on the surface of the biological tissue of the subject.

The present invention is not limited to the above-described embodiment, and of course, various modifications and applications can be implemented within a scope without departing from the gist of the invention. Furthermore, the above-described embodiment includes the invention in various stages, and various inventions may be extracted by appropriate combinations in the plurality of disclosed constituent elements. For example, in a case where the problem to be solved by the invention can be solved and advantages of the invention are attained even when some constituent elements are deleted from all the constituent elements illustrated in the above-described one embodiment, the configuration from which the constituent elements are deleted may be extracted as the invention. Furthermore, constituent elements across different embodiments may also be appropriately combined. This invention is not restricted by a specific embodiment of the invention except for the limitation by the accompanying claims.

What is claimed is:

1. A heat invasion observation apparatus comprising:
   a fluorescence image generation circuit configured to:
   obtain an image pickup signal by picking up an image of fluorescence generated from a heat invasion area in biological tissue irradiated with exciting light for exciting a substance contained in the heat invasion area;
   generate fluorescence image data based on the obtained image pickup signal, wherein:
   the substance is generated when the biological tissue is thermally processed; and
   a storage apparatus that stores relationship information in advance which indicates a correlation relationship between a fluorescence intensity calculated from the fluorescence image data and an invasion depth by heat in the biological tissue at which a fluorescence intensity is generated, wherein:
   an information generation circuit configured to generate, as the information related to the heat invasion area, heat invasion depth information based on fluorescence intensity information calculated from the fluorescence image data and the relationship information stored in the storage apparatus.

2. The heat invasion observation apparatus according to claim 1, wherein
the fluorescence image generation circuit is configured to pick up an image of light including band components at 500 to 600 nm generated from the heat invasion area.

3. The heat invasion observation apparatus according to claim 1, wherein:
the information generation circuit is configured to generate information related to the heat invasion area based on the fluorescence image data.

4. The heat invasion observation apparatus according to claim 3, wherein
the information generation circuit generates the information related to the heat invasion area based on fluorescence intensity information extracted from the fluorescence image data.

5. The heat invasion observation apparatus according to claim 3, wherein
the information related to the heat invasion area is heat invasion range information including location information of a range of an area of heat invasion.

6. The heat invasion observation apparatus according to claim 5, further comprising:
a white light image generation circuit configured to:
irradiate the biological tissue with white light;
obtain an image pickup signal generated by picking up an image of return light from the biological tissue irradiated with white light; and
generate white light image data based on the obtained image pickup signal, wherein the heat invasion range information is information indicating an area where fluorescence at a predetermined fluorescence intensity or higher is generated in the area where the fluorescence image data is configured to obtain the image pickup signal; and
a display image generation circuit configured to generate, based on the white light image data and the heat invasion range information, display image data in which the area where the fluorescence at the predetermined fluorescence intensity or higher is generated is processed and emphasized.

7. The heat invasion observation apparatus according to claim 6, wherein
the display image generation circuit configured to generate the display image data based on the fluorescence image data and the information related to the heat invasion area.

8. The heat invasion observation apparatus according to claim 5, further comprising an energy device configured to cauterize the biological tissue to mark the heat invasion area, wherein:
the heat invasion range information indicates a high fluorescence area where a predetermined fluorescence intensity or higher is generated in an area where the fluorescence image data is configured to obtain the image pickup signal.

9. The heat invasion observation apparatus according to claim 5, further comprising:
a white light image generation circuit configured to obtain an image pickup signal generated by picking up an image of return light from the biological tissue irradiated with white light, and generate white light image data based on the obtained image pickup signal; and
a display image generation circuit configured to generate display image data based on the white light image data and the information related to the heat invasion area.

10. The heat invasion observation apparatus according to claim 3, wherein
the information generation circuit generates, as the information related to the heat invasion area and generated based on fluorescence intensity information calculated from the fluorescence image data,
heat invasion range information including location information of an area of heat invasion; and
heat invasion degree distribution information including a distribution of fluorescence intensities generated from respective locations in the heat invasion area,
the heat invasion observation apparatus further comprising:
a white light image generation circuit configured to obtain an image pickup signal generated by picking up an image of return light from the biological tissue irradiated with white light, and generate white light image data based on the obtained image pickup signal; and
a display image generation circuit configured to generate display image data based on the white light image data, the heat invasion range information, and the heat invasion degree distribution information.

11. The heat invasion observation apparatus according to claim 1, wherein
the fluorescence image generation circuit generates pre-treatment fluorescence image data before the biological tissue is treated by an energy device, and post-treatment fluorescence image data after the biological tissue is treated by the energy device,
the heat invasion observation apparatus further comprising:
an information generation circuit configured to extract difference information of fluorescence intensities that change before and after the biological tissue is processed by the energy device based on the pre-treatment fluorescence image data and the post-treatment fluorescence image data, and generate heat invasion information from the extracted difference information of fluorescence intensities.

12. The heat invasion observation apparatus according to claim 1, wherein
the relationship information is information indicating a positive correlation indicating that the invasion depth by the heat in the biological tissue at which the fluorescence intensity is generated is deeper as the fluorescence intensity is more intense.

13. The heat invasion observation apparatus according to claim 1, further comprising:
a display image generation circuit configured to generate display image data based on the fluorescence image data and the heat invasion depth information.

14. The heat invasion observation apparatus according to claim 1, further comprising:
a white light image generation circuit configured to obtain an image pickup signal generated by picking up an image of return light from the biological tissue irradiated with white light, and generate white light image data based on the obtained image pickup signal; and
a display image generation circuit configured to generate display image data based on the white light image data and the heat invasion depth information.

15. The heat invasion observation apparatus according to claim 1, wherein
the heat invasion depth information generated by the information generation circuit is a heat invasion depth in a predetermined area that is decided in advance, the heat invasion observation apparatus further comprising:
- a white light image generation circuit configured to obtain an image pickup signal generated by picking up an image of return light from the biological tissue irradiated with white light, and generate white light image data based on the obtained image pickup signal; and
- a display image generation circuit configured to generate display image data based on the white light image data and the heat invasion depth information.

16. The heat invasion observation apparatus according to claim 1, wherein
the information generation circuit generates, as the information related to the heat invasion area and generated based on the fluorescence intensity information calculated from the fluorescence image data,
heat invasion range information including location information of an area of heat invasion; and
heat invasion degree distribution information including a distribution of fluorescence intensities generated from respective locations in the heat invasion area,
the heat invasion observation apparatus further comprising:
- a white light image generation circuit configured to obtain an image pickup signal generated by picking up an image of return light from the biological tissue irradiated with white light, and generate white light image data based on the obtained image pickup signal; and
- a display image generation circuit configured to generate display image data based on the white light image data, the heat invasion range information, the heat invasion degree distribution information, and the heat invasion depth information.

17. The heat invasion observation apparatus according to claim 1, wherein
the fluorescence image generation circuit is configured to sequentially generate the fluorescence image data based on sequentially inputted image pickup signals,
the heat invasion observation apparatus further comprising:
- an information generation circuit configured to sequentially calculate information related to an intensity of fluorescence generated from the heat invasion area based on the fluorescence image data sequentially generated by the fluorescence image generation circuit, and generate fluorescence intensity information;
- a determination circuit configured to determine whether or not the intensity of the fluorescence generated from the heat invasion area is equal to or higher than a predetermined threshold based on the fluorescence intensity information sequentially generated by the information generation circuit; and
- an announcement apparatus configured to issue an announcement based on a result determined by the determination circuit.

18. The heat invasion observation apparatus according to claim 17, wherein
the announcement apparatus issues the announcement when a heat invasion depth in a predetermined area in an area observed by the fluorescence image data reaches a predetermined depth or more based on heat invasion depth information.

19. The heat invasion observation apparatus according to claim 17, wherein
the announcement apparatus issues the announcement when a heat invasion depth in at least a partial area in an area observed by the fluorescence image data reaches a predetermined depth or more based on heat invasion depth information.

20. A heat invasion observation apparatus comprising:
a fluorescence image generation circuit configured to:
- obtain an image pickup signal by picking up an image of fluorescence generated from a heat invasion area in biological tissue irradiated with exciting light for exciting a substance contained in the heat invasion area;
- generate fluorescence image data based on the obtained image pickup signal, wherein:
  the substance is generated when the biological tissue is thermally processed;
- generate pre-treatment fluorescence image data before the biological tissue is treated by an energy device, and post-treatment fluorescence image data after the biological tissue is treated by the energy device; and
an information generation circuit configured to extract difference information of fluorescence intensities that change before and after the biological tissue is processed by the energy device based on the pre-treatment fluorescence image data and the post-treatment fluorescence image data, and generate heat invasion information from the extracted difference information of fluorescence intensities.

21. The heat invasion observation apparatus according to claim 20, wherein
the fluorescence image generation circuit is configured to pick up an image of light including band components at 500 to 600 nm generated from the heat invasion area.

22. The heat invasion observation apparatus according to claim 20, further comprising:
an information generation circuit configured to generate information related to the heat invasion area based on the fluorescence image data.

23. The heat invasion observation apparatus according to claim 22, wherein
the information generation circuit generates the information related to the heat invasion area based on fluorescence intensity information extracted from the fluorescence image data.

24. The heat invasion observation apparatus according to claim 22, wherein
the information related to the heat invasion area is heat invasion range information including location information of a range of an area of heat invasion.

25. The heat invasion observation apparatus according to claim 24, further comprising:
- a white light image generation circuit configured to:
  irradiate the biological tissue with white light;
  obtain an image pickup signal generated by picking up an image of return light from the biological tissue irradiated with white light; and
  generate white light image data based on the obtained image pickup signal, wherein the heat invasion range information is information indicating an area where fluorescence at a predetermined fluorescence intensity or higher is generated in the area where the fluorescence image data is configured to obtain the image pickup signal; and
- a display image generation circuit configured to generate, based on the white light image data and the heat invasion range information, display image data in which the area where the fluorescence at the predetermined fluorescence intensity or higher is generated is processed and emphasized.

26. The heat invasion observation apparatus according to claim 24, further comprising an energy device configured to cauterize the biological tissue to mark the heat invasion area, wherein:

the heat invasion range information indicates a high fluorescence area where a predetermined fluorescence intensity or higher is generated in an area where the fluorescence image data is configured to obtain the image pickup signal.

27. A heat invasion observation apparatus comprising:
a processor configured to:
obtain an image pickup signal based on an image of fluorescence generated from a heat invasion area in a biological tissue, the heat invasion area containing a substance generated when the biological tissue is thermally processed;
generate fluorescence image data based on the image pickup signal;
calculate fluorescence intensity information based on the fluorescence image data;
receive a relationship information indicating a correlation relationship between a fluorescence intensity and an invasion depth by heat in a biological tissue; and
generate heat invasion depth information based on the fluorescence intensity information and the relationship information.

28. The heat invasion observation apparatus according to claim 27, further comprising:
an information generation circuit configured to generate information related to the heat invasion area based on the fluorescence image data.

29. The heat invasion observation apparatus according to claim 28, wherein
the information generation circuit generates the information related to the heat invasion area based on fluorescence intensity information extracted from the fluorescence image data.

* * * * *